(12) United States Patent
Mielgo et al.

(10) Patent No.: US 9,476,068 B2
(45) Date of Patent: Oct. 25, 2016

(54) HIGH EFFICIENCY PROCESS AND HIGH PROTEIN FEED CO-PRODUCT

(75) Inventors: Iñaki Mielgo, Sevilla (ES); Patrick Mulvihill, Weldon Spring, MO (US)

(73) Assignee: Abengoa Bioenergy New Technologies, LLC, Chesterfield, MO (US)

( * ) Notice: Subject to any disclaimer, the term of this patent is extended or adjusted under 35 U.S.C. 154(b) by 194 days.

(21) Appl. No.: 13/266,231

(22) PCT Filed: Nov. 4, 2010

(86) PCT No.: PCT/US2010/055478
§ 371 (c)(1),
(2), (4) Date: Oct. 25, 2011

(87) PCT Pub. No.: WO2011/056991
PCT Pub. Date: May 12, 2011

(65) Prior Publication Data
US 2012/0045545 A1    Feb. 23, 2012

Related U.S. Application Data

(60) Provisional application No. 61/257,951, filed on Nov. 4, 2009.

(51) Int. Cl.
A23L 1/10       (2006.01)
A23L 1/28       (2006.01)
(Continued)

(52) U.S. Cl.
CPC ............... *C12P 7/10* (2013.01); *A23K 1/007* (2013.01); *A23K 1/146* (2013.01); *C12P 7/08* (2013.01); *C12P 7/14* (2013.01); *A21D 2/36* (2013.01); *Y02E 50/16* (2013.01)

(58) Field of Classification Search
CPC ........ A23K 1/003; A23K 1/164; A23K 1/14; A23K 1/188; A23K 1/007; A23K 1/146; C12P 7/40; C12P 7/10; C12P 7/08; C12N 1/14; A21D 2/36; A21D 13/02; C12G 3/02; C12C 11/003; C12C 11/07
USPC .............................. 426/31, 14, 463, 493, 11
See application file for complete search history.

(56) References Cited

U.S. PATENT DOCUMENTS 3,236,740 A    2/1966 Smith et al.
4,200,692 A    4/1980 Puls et al.
(Continued)

FOREIGN PATENT DOCUMENTS

WO    0238787 A2     5/2002
WO    2004018645 A2  3/2004
(Continued)

OTHER PUBLICATIONS

"Liquozyme SC DS" Available online at www.bioenergy.novozymes.com on Aug. 22, 2007.*
(Continued)

*Primary Examiner* — Erik Kashnikow
*Assistant Examiner* — Assaf Zilbering
(74) *Attorney, Agent, or Firm* — Armstrong Teasdale LLP

(57) ABSTRACT

A process is disclosed for producing a feed co-product by ethanol fermentation of plant matter comprising starch and another polysaccharide selected from the group consisting of hemicellulose and cellulose. The process comprises: (i) carrying out a primary fermentation process, distilling the primary fermentation mixture to form a primary feed co-product derived from the fermentation of the primary fermentation mixture and a primary distillate product comprising ethanol and (ii) carrying out a secondary fermentation process and distilling the secondary fermentation mixture to form the modified feed co-product and a secondary distillate product comprising ethanol.

13 Claims, 1 Drawing Sheet

(51) Int. Cl.

| | |
|---|---|
| C12C 3/08 | (2006.01) |
| C12C 3/12 | (2006.01) |
| C12C 7/00 | (2006.01) |
| C12C 11/00 | (2006.01) |
| C12G 3/08 | (2006.01) |
| C12P 7/10 | (2006.01) |
| A23K 1/14 | (2006.01) |
| A23K 1/00 | (2006.01) |
| C12P 7/08 | (2006.01) |
| C12P 7/14 | (2006.01) |
| A21D 2/36 | (2006.01) |

(56) References Cited

U.S. PATENT DOCUMENTS

| | | | |
|---|---|---|---|
| 4,376,163 A * | 3/1983 | Ehnstrom | 435/162 |
| 4,752,579 A | 6/1988 | Arena et al. | |
| 4,806,475 A | 2/1989 | Gould | |
| 4,822,737 A | 4/1989 | Saida | |
| 5,047,332 A | 9/1991 | Chahal | |
| 5,177,008 A | 1/1993 | Kampen | |
| 5,487,989 A | 1/1996 | Fowler et al. | |
| 5,705,369 A | 1/1998 | Torget et al. | |
| 5,733,758 A | 3/1998 | Nguyen | |
| 5,932,452 A | 8/1999 | Mustranta et al. | |
| 6,090,595 A | 7/2000 | Foody et al. | |
| 6,444,437 B1 | 9/2002 | Sporleder et al. | |
| 6,569,653 B1 | 5/2003 | Alard et al. | |
| 6,927,048 B2 | 8/2005 | Verser et al. | |
| 2003/0044951 A1 | 3/2003 | Sporleder et al. | |
| 2006/0233864 A1 | 10/2006 | Power | |
| 2007/0037267 A1 | 2/2007 | Lewis et al. | |
| 2007/0218530 A1 | 9/2007 | Duck et al. | |
| 2007/0250961 A1 | 10/2007 | Blaylock et al. | |
| 2011/0008489 A1 | 1/2011 | Robb et al. | |

FOREIGN PATENT DOCUMENTS

| | | |
|---|---|---|
| WO | 2004081193 A2 | 9/2004 |
| WO | 2004103086 A2 | 12/2004 |
| WO | 2005079190 A2 | 9/2005 |
| WO | 2009079183 A1 | 6/2009 |
| WO | 2011056991 A1 | 5/2011 |

OTHER PUBLICATIONS

European Search Report and European Search Opinion issued in related European Patent Application No. 10829102.2 dated Nov. 30, 2012; 10 pgs.

Al-Suwaiegh, S., et al., "Utilization of Distillers Grains from the Fermentation of Sorghum or Corn in Diets for Finishing Beef and Lactating Dairy Cattle," 2002, J Anim Sci, 80:1105-1111.

Armentano, L., "How Can we Optimize the Protein Quality Delivered to Lactating Cows When feeding DDGS?," 1994, Proceedings Distillers Feed Research Council, 49:63-68.

Armentano, L.E., "Altered Milk Production Due to Changes in Protein Quality for Diets Based on Distillers Grains with Solubles," 1994, J. Dairy Sci., 72(Suppl 1):244.

De Menezes, T.J.B., "The Treatment and Utilization of Alcohol Stillage," 1989, International Biosystems, vol. III, pp. 1-14, D.L. Wise, editor, CRC Press, Boca Raton, Florida, USA.

Dien, et al., "Conversion of Corn Fiber to Ethanol by Recombinant E. coli Strain FBR3," 1999, J Ind Microbio Biotech, 22:575-581.

Elander, R.T., "Executive Summary New Energy Company of Indiana/National Renewable Energy Lab (NREL) Co-Op Research and Development Agreement (CRADA) Completed 1997," Public Release 1999, NREL, Golden, Colorado, USA, 11 pages.

Ghose, T.K., "Measurement of Cellulase Activities," 1987, Pure and Appl Chem, 59/2:257-268.

Gulati, et al., "Assessment of Ethanol Production Options for Corn Products," 1996, Biores Technol, 58:253-264.

Irwin, et al., "Corn Fiber Hydrolysis by Themobifida Fusca Extracellular Enzymes," 2003, Appl Microbiol Biotechnol, 61:352-358.

Lardy, G., "Feeding Coproducts of the Ethanol Industry to Beef Cattle," 2007, NSDU Extension Service, 8 pages.

Leathers, T.D., "Bioconversions of Maize Residues to Value-Added Coproducts Using Yeast-like Fungi," 2003, FEMS Yeast Research, 3:133-140.

Liu, C., et al., "Corn Distillers Grains versus a Blend of Protein Supplements with or without ruminally Protected Amino Acids for Lactating Cows," 2000, J Dairy Sci, 83:2075-2084.

Nichols, J.R., et al., "Evaluation of Corn Distillers Grains and Ruminally Protected Lysine and Methionine for Lactating Dairy Cows," 1998, J Dairy Sci, 81:482-491.

Reeve, A., "Chapter 4 Starch Hydrolysis: Processes and Equipment," 1992, Starch Hydrolysis Products Worldwide Technology, Production, and Applications, F.W. Schenck and R. E. Hebeda, editors, VCH (Wiley), New York, New York, USA, pp. 79-120.

Schingoethe, D.J., et al., "Milk Production and Composition from Cows Fed Wet corn Distillers Grains," 1999, J. Dairy Sci, 82:574-580.

Singh, V., et al, "A Comparison Between Conversion of Pericarp and Endosperm Fiber from Corn into Ethanol," 2004, Paper No. 046056, 2004 ASAE Annual Meeting, 15 pages http://asae.frymulti.com/abstract.asp?aid=17111&t=2//.

Teleman, A., et al., "Progress-Curve Analysis Shows that Glucose Inhibits the Cellotriose Hydrolysis Catalysed by Cellobiohydrolase II from Trichoderma Reesei," 1995, Eur J Biochem, 231:250-258.

Wilkie, A.C., et al., "Stillage Characterization and Anaerobic Treatment of Ethanol Stillage from Conventional and Cellulosic Feedstock," 2000, Biomass & Bioenergy, 19:63-102.

Wu, Y.V., "Protein-Rich Residue from Ethanolic Fermentation of High-Lysine, Dent, Waxy, and White Corn Varieties," 1989, Cereal Chem, 66/6:506-509.

Abstract of CN 1151834A, published Jun. 18, 1997—Luzhoulaojiao Co Ltd, 1 page.

Abstract of CN 1208077A, published Feb. 17, 1999—Nie Guilan, 1 page.

International Search Report and Written Opinion for corresponding International Application No. PCT/US10/55478, dated Mar. 11, 2011, 15 pages.

* cited by examiner

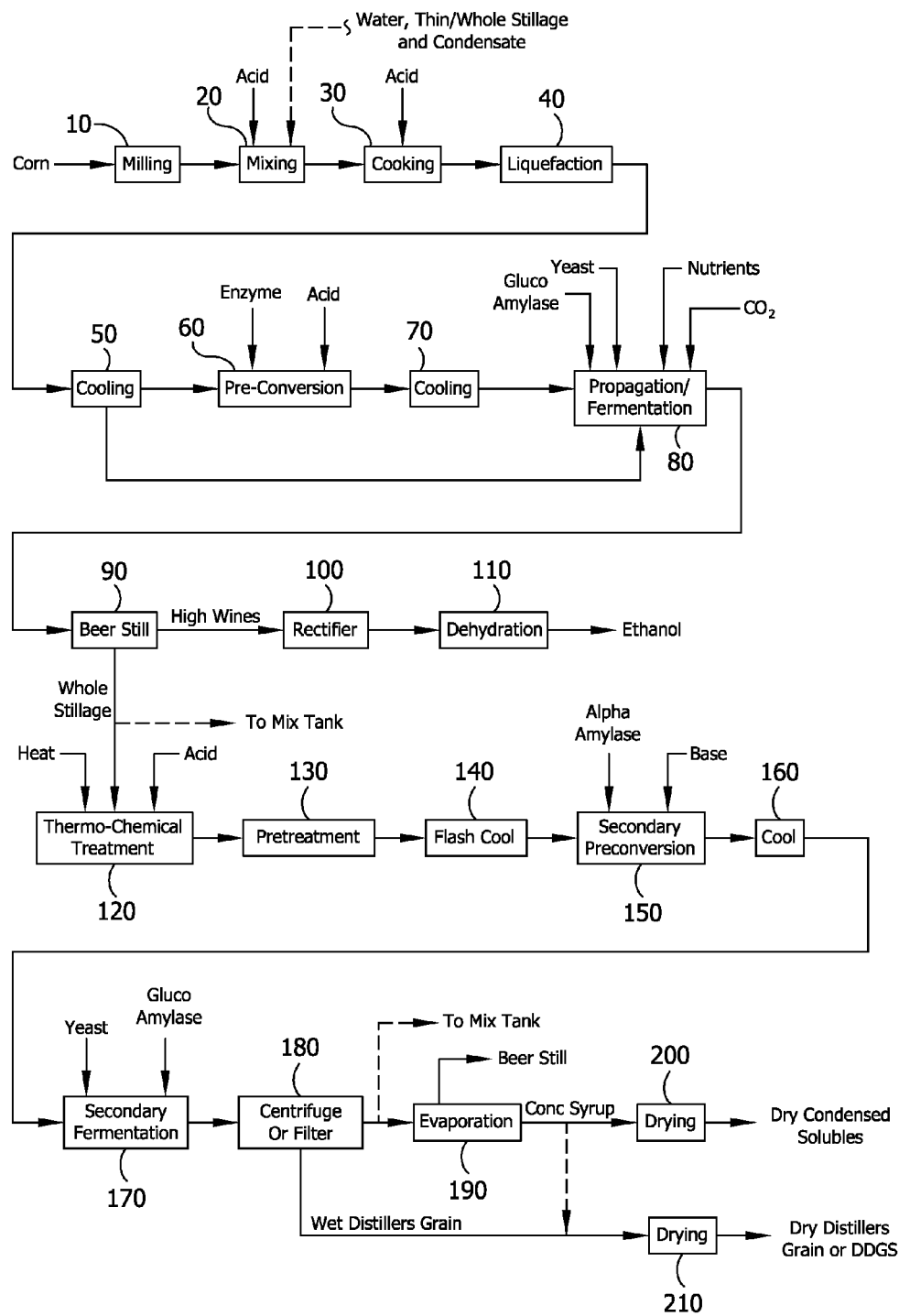

HIGH EFFICIENCY PROCESS AND HIGH PROTEIN FEED CO-PRODUCT

REFERENCE TO RELATED APPLICATIONS

This application is a United States National Stage Application based on International Patent Application No. PCT/US2010/055478, filed Nov. 4, 2010, and claims the benefit of U.S. Provisional Patent Application Ser. No. 61/257,951, filed Nov. 4, 2009, the entire contents of which are incorporated herein by reference.

GOVERNMENT LICENSE RIGHTS

This invention was made with Government support under DOE Cooperative Agreement No. DE-FC36-03GO13142. The Government has certain rights in this invention.

FIELD OF THE INVENTION

The present invention relates to a process for obtaining high ethanol yield from the fermentation of the energy crop and for producing a nutritionally enhanced feed co-product.

BACKGROUND OF THE INVENTION

Ethanol and a corresponding feed co-product may be produced from a variety of feedstocks using any conventional dry mill or wet mill fermentation process known in the art. See for example, CORN, Chemistry and Technology, Stanley A. Watson and Paul E. Ramstad, editors, Published by the American Association of Cereal Chemists, Inc., St. Paul, Minn., USA, the entire contents of which are incorporated herein by reference.

Ethanol produced from fermentation of cereal grains yields co-products that are useful as animal feeds. Some of these feed co-products are known in the art as Wet Distillers Grains (WDG), Dried Distillers Grains (DDG), Wet Distillers Grains Plus Solubles (WDGS), or Dried Distillers Grains plus Solubles (DDGS). Removal of the starch component during fermentation concentrates the original protein, mineral, vitamin, fiber, and fat content. For example, dry mill ethanol production uses the starch portion of corn kernels, which is about 70% of the kernel. The starch component is converted by enzymatic hydrolysis to sugars which are then fermented to form ethanol. The ethanol is recovered by distillation. The remaining nutrients are concentrated into wet distillers grains (WDG) or Wet Distillers Grains Plus Solubles (WDGS). The WDG or WDGS may be used directly as a feed co-product or may be dried to form dried distillers grains (DDG) or dried distillers grains plus solubles (DDGS). Drying increases shelf life and improves transportability.

These grain products, as well as condensed distillers solubles (CDS) and dried distillers solubles (DDS), have been used in dairy rations for over a century. Research conducted over the past 50 years comparing these products to other protein and energy feeds has proven their value. See Armentano 1994 & 1996; Nichols et al. 1998; Schingoethe et al., 1999; Liu et al., 2000 and Al-Suwaiegh et al., 2002. DDGS has become a common component of commercial dairy protein supplements, often comprising 25-35% of the blend (dry matter basis) depending upon the price of the other ingredients. A common comparison by dairy nutritionists is that one pound of DDGS is roughly equivalent to 0.6 pounds of shelled corn and 0.4 pounds of soybean meal.

Among the grain feed components, protein has the highest value commercially while fiber has the least value. Although the nutritional value of grain feed products may vary slightly according to its source (e.g., corn, sorghum (milo), sugar beets) and crop quality, these are essentially commodity products. Accordingly, a method for improving the quality and value (i.e., increased protein content and/or decreased fiber content) of grain feed co-products resulting from ethanol production is desirable to produce grain feed products having enhanced nutritional value as compared to the grain feed products currently available from the commodity markets.

SUMMARY OF THE INVENTION

Briefly, therefore, the present invention is directed to a process for producing a modified feed co-product by ethanol fermentation of plant matter. The process comprises forming an acidic aqueous medium comprising plant matter and having a pH from about 2 to about 6. The plant matter comprises starch and another polysaccharide selected from the group consisting of hemicellulose and cellulose. The process comprises hydrolyzing at least a portion of the starch, said another polysaccharide, or both in the medium at a temperature of at least about 85° C. The process comprises contacting at least a portion of the starch in the acidic aqueous medium with α-amylase which catalyzes enzymatic hydrolysis of at least a portion of the starch to yield simple sugars having from one to three saccharide units. The process comprises contacting the additional polysaccharide in the acidic aqueous medium with a primary pre-conversion enzyme selected from the group consisting of xylanase, cellulase, hemicellulase, and combinations thereof. The primary pre-conversion enzyme catalyzes enzymatic hydrolysis of at least a portion of the additional polysaccharide to yield a primary enzymatic hydrolyzate containing additional simple sugars having from one to four saccharide units. The process comprises combining the primary enzymatic hydrolysate and yeast to thereby form a primary fermentation mixture. During primary fermentation, at least a portion of the simple sugars produced by hydrolysis of starch and another polysaccharide are converted by fermentation to produce ethanol.

The process comprises distilling the primary fermentation mixture to separate at least a portion of the ethanol. Distillation forms: (i) a primary distillate product comprising ethanol; and (ii) a primary feed co-product derived from the fermentation of the primary fermentation mixture. The primary feed co-product comprises polysaccharide remaining therein.

The process comprises forming an acidified primary feed co-product by adjusting the pH of the primary feed co-product to between about 2 and about 6. The process comprises forming a hydrolyzed primary feed co-product. The hydrolyzed primary feed co-product is formed by hydrolyzing at least a portion of the polysaccharide remaining in acidified primary feed co-product at a temperature of at least about 85° C. The process comprises combining the hydrolyzed primary feed co-product, a secondary pre-conversion enzyme, and a pH adjusting agent to form a secondary enzymatic hydrolysate having a pH from about 4 to about 6.5. The secondary pre-conversion enzyme is selected from the group consisting of amylase, xylanase, cellulase, hemicellulase, and combinations thereof. The secondary pre-conversion enzyme catalyzes enzymatic hydrolysis of at least a portion of the polysaccharide remaining in the secondary enzymatic hydrolysate to produce a third crop of simple sugars having from one to four saccharide units. The process comprises adding yeast to the secondary enzymatic hydrolysate to form a secondary fermentation mixture. During secondary fermentation, at least a portion of the simple sugars contained therein are converted by fermentation to produce ethanol. The process comprises distilling the secondary fermentation mixture to separate at least a portion of the ethanol thereby forming (i) the modified feed co-product and (ii) a secondary distillate product comprising ethanol.

The present invention is further directed to a method for enhancing the conversion of starch from plant matter into ethanol. The process comprises combining water, a milled plant matter feedstock, and whole stillage derived from the ethanol fermentation of a plant matter feedstock to thereby form an aqueous medium having a pH between about 2 and about 6. The milled plant matter feedstock, the whole stillage, or both comprise starch and another polysaccharide selected from the group consisting of hemicellulose, cellulose, and combinations thereof. The process comprises gelatinizing at least a portion of the starch in the aqueous medium at a temperature of at least about 100° C. to thereby form a gelatinized medium. The process comprises contacting at least a portion of gelatinized starch in the gelatinized medium with α-amylase. The α-amylase catalyzes enzymatic hydrolysis of at least a portion of the gelatinized starch to thereby form a liquefied medium comprising fermentable sugars. The process comprises contacting the liquefied medium with glucoamylase and yeast to thereby form a primary fermentation medium. During primary fermentation, at least a portion of the fermentable sugars are converted by fermentation to produce ethanol. The process comprises distilling the primary fermentation medium to separate at least a portion of the ethanol thereby forming: (i) a primary distillate product comprising ethanol; and (ii) a primary feed co-product derived from the fermentation of the primary fermentation medium.

The present invention is still further directed to a process for ethanol fermentation of plant matter. The process comprises forming an acidic aqueous medium comprising plant matter. The plant matter comprises starch and another polysaccharide selected from the group consisting of hemicellulose and cellulose. The process comprises hydrolyzing at least a portion of the starch, another polysaccharide, or both in the acidic aqueous medium. The process comprises contacting at least a portion of the starch in acidic aqueous medium with α-amylase which catalyzes enzymatic hydrolysis of at least a portion of the starch to yield simple sugars having from one to three saccharide units to thereby form a liquefied medium. The process comprises continuously combining the liquefied medium and a glucoamylase. The process comprises combining the liquefied medium, the glucoamylase and yeast to thereby form a fermentation mixture, wherein at least a portion of the simple sugars produced by hydrolysis of starch and another polysaccharide are converted by fermentation to produce ethanol.

The present invention is still further directed to a process for ethanol fermentation of plant matter. The process comprises forming an acidic aqueous medium comprising plant matter. The plant matter comprises starch and another polysaccharide selected from the group consisting of hemicellulose and cellulose. The process comprises hydrolyzing at least a portion of the starch, another polysaccharide, or both in acidic aqueous medium. The process comprises contacting at least a portion of the starch in acidic aqueous medium with α-amylase which catalyzes enzymatic hydrolysis of at least a portion of the starch to yield simple sugars having from one to three saccharide units to thereby form a liquefied medium. The process comprises combining the liquefied medium and a glucoamylase to thereby form a saccharification mixture. The process comprises combining the saccharification mixture and a yeast to thereby form a fermentation mixture, wherein at least a portion of the simple sugars produced by hydrolysis of said starch and said another polysaccharide are converted by fermentation to produce ethanol.

The present invention is still further directed to a process for ethanol fermentation of plant matter. The process comprises forming an acidic aqueous medium comprising plant matter. The plant matter comprises starch and another polysaccharide selected from the group consisting of hemicellulose and cellulose. The process comprises hydrolyzing at least a portion of the starch, another polysaccharide, or both in the acidic aqueous medium. The process comprises contacting at least a portion of the starch in the acidic aqueous medium with α-amylase which catalyzes enzymatic hydrolysis of at least a portion of the starch to yield simple sugars having from one to three saccharide units to thereby form a liquefied medium. The process comprises propagating yeast. Propagation comprises combining the yeast, a portion of the liquefied medium, and glucoamylase to thereby form a propagation mixture. The propagation mixture is aerated. The process comprises combining glucoamylase, the liquefied medium, and the propagation mixture to thereby form a fermentation mixture, wherein at least a portion of the simple sugars produced by hydrolysis of starch and another polysaccharide are converted by fermentation to produce ethanol.

Other objects and features will be in part apparent and in part pointed out hereinafter.

BRIEF DESCRIPTION OF THE DRAWINGS

FIG. 1 is a flowchart depicting an embodiment of the process of the present invention.

Corresponding reference characters indicate corresponding parts throughout the drawings.

DESCRIPTION OF THE EMBODIMENT(S) OF THE INVENTION

The present invention is generally directed to the ethanol fermentation of plant matter. In one aspect, the present invention is directed to a method for enhancing the conversion of starch in an energy crop into fermentable sugar. In another aspect, the present invention is directed to a method for increasing the ethanol yield of fermentation of starch in an energy crop. In yet another aspect, the present invention is directed to a method for converting non-fermentable polysaccharides in an energy crop into fermentable sugar. In yet another aspect, the present invention is directed to increasing the ethanol yield of fermentation of an energy crop by increasing the relative amount of fermentable sugars by converting non-fermentable polysaccharides in an energy crop into fermentable sugars. In still another aspect, the present invention is directed to a method for producing a feed co-product of improved nutritional quality.

In one aspect, the process enhances the conversion of starch into fermentable sugars, which may thereby enhance the efficiency of the fermentation of starch from an energy crop to ethanol. In another aspect, the process of the present invention enables the conversion of other complex polysaccharides into fermentable sugars, which may then be fermented into ethanol. In conventional methods, these complex polysaccharides (e.g., cellulose, hemicellulose, and other fibers such as lignin-cellulose complex and lignin-hemicellulose complex) typically provide little or no fermentable sugar substrate to the ethanol fermentation process and remain part of the whole stillage animal feed co-product. According to some embodiments of the process of the present invention, at least a portion of these complex polysaccharides is converted to fermentable sugars. The fermentable sugars may be fermented into ethanol thereby enhancing the ethanol yield. Separation of ethanol from the fermentation product yields a whole stillage product having enhanced protein content and reduced fiber content.

The present invention is therefore additionally directed to a process for forming an improved feed co-product derived from ethanol fermentation of an energy crop. By converting at least a portion of complex polysaccharides of little nutritive value in the energy crop into fermentable sugars and fermenting at least a portion of the fermentable sugars to produce ethanol, the process of the present invention yields a whole stillage feed co-product comprising enhanced concentrations of the components of high nutritional quality, e.g. protein and oil, and reduced concentrations of complex polysaccharides of little nutritive value, e.g., hemicellulose and cellulose. The present invention is therefore further directed to the enhanced feed co-product having enhanced nutritive value as compared to the grain feed products currently available from the commodity markets. The enhanced feed co-product exhibits improved protein and oil content and lesser polysaccharide content having little nutritive value. Since the nutritionally enhanced feed co-products of the present invention have improved nutritional quality compared to conventional feed co-products, such as conventional dried distillers grains, it is believed the process of the present invention increases the commercial value of the feed co-product thereby enhancing the profitability of the overall ethanol production process. The feed co-product of the present invention may be utilized as a high quality feed for all animal feed applications. For example, the product of the present invention may be utilized as a feed for monogastric animals and may even be used for human consumption.

The feedstock is preferably a plant-based feed stock derived from an energy crop. As is known in the art, an energy crop is a plant whose fruits and/or seeds may be used in the production of biofuels. Exemplary energy crops include corn, millet, white sweet-clover and so on. The fruits and/or seeds of an energy crop typically comprise a large portion of starch, which is readily fermentable into ethanol by conventional processes. The feedstock used in the process of the present invention may be any feed stock comprising at least about 40% by weight, preferably at least about 50% by weight of a carbohydrate, such as a starch or sugar, which is fermentable into ethanol. A corn kernel, for example, typically comprises about 70% by weight starch on a dry basis. Sorghum (milo) also contains about 70% by weight starch. Wheat contains about 65% by weight starch. Rye contains about 58% by weight starch. Barley contains about 51% by weight starch.

Typical energy crops include the "true grasses" (from the family Poaceae), but other energy crops may be used, such as vegetables commonly referred to as tubers and sugar beet (from the family Amaranthaceae). The fruits and seeds (e.g., corn kernels, wheat berries—with or without the hull, oat groats—with or without the hull, etc.) of energy crops typically contain protein, oil, and complex polysaccharides, chief among them, starch, cellulose, hemicellulose, and other fibers, such as lignin-cellulose complex and lignin-hemicellulose complex. Conventionally, starch is the most important energy source in ethanol fermentation, whereby starch is enzymatically hydrolyzed to glucose, which is converted by yeast into ethanol and carbon dioxide.

Plant matter feedstocks derived from the Poaceae family (the "true grasses") comprise the fruits and/or seeds of the cereal grains including corn, maize, oats, grain sorghum, milo, wheat, barley, triticale, rice, millet, rye, and buckwheat. Additional true grasses include bamboo, marram grass, meadow grass, reed, ryegrass, sugar cane, and grasses from the *Miscanthus* genus.

The plant matter feedstocks may also be derived from "tubers," including potatoes, cassava, sweet potato, and yam.

Plant matter feedstocks may be derived from the Amaranthaceae family, including sugar beet, amaranth, and quinoa. Other plant matter feedstocks include willows from the *Salix* genus and flowering plants from the *Populus* genus, both classified in the Salicaceae family.

More typically, the plant matter feedstock is derived from corn, grain sorghum, wheat, sugarcane, and/or sugar beets, potatoes, and cassava. More typically, the plant matter feedstock is derived from corn, specifically, the corn kernel.

The energy crops for use in the process of the present invention are suitable plant matter feedstocks since they comprise sugars, including starch, and fibers, such as cellulose and hemicellulose that are or may be treated to yield simple sugar substrates suitable for ethanol fermentation. Starches typically comprise two components: amylose and amylopectin. Amylose is a polysaccharide that may comprise up to several thousand glucose units, more typically comprising from about 300 to about 3000 glucose units in alpha linkages. Amylose is characterized by relatively little branching, such that the main linkage is $\alpha(1 \rightarrow 4)$, which promotes formation of a helical structure. Amylopectin is a polysaccharide typically comprising from about 2000 to about 20,000 glucose units in alpha linkages. Unlike amylose, amylopectin is highly branched and comprises linear portions in $\alpha(1 \rightarrow 4)$ linkages with branching taking place through $\alpha(1 \rightarrow 6)$ linkages about every 24 to 30 glucose units. Plants store amylopectin and amylose as starch granules in amyloplasts. Certain varieties of plants are "waxy," meaning that the starch granules have no amylose.

Cellulose is a structural, linear polysaccharide of the plant cell wall, and it contains anywhere from several hundred to over ten thousand glucose units in $\beta(1 \rightarrow 4)$ linkages. Cellulose is a major component of energy crops. Hemicelluloses are heteropolymers also present in cell walls, and its polysaccharides include glucose, xylose, mannose, galactose, rhamnose, and arabinose. Since hemicellulose is a random, amorphous polymer, it provides little strength and is easily hydrolyzed by dilute acid or base and a variety of hemicellulase enzymes. Hemicellulose typically comprises about 200 saccharide units. Hemicelluloses include xylan, glucuronoxylan, arabinoxylan, glucomannan, and xyloglucan. Hemicellulose is covalently linked to lignin, a complex, cross-linked, polymeric macromolecule that fills the spaces in cell walls between the cellulose, hemicellulose, and pectin components.

Preferably, the plant matter feedstock is storage grain which has been dried to an extent that inhibits microbial action (i.e., spoilage) and allows for long term storage.

An embodiment of the process of the present invention is generally depicted in FIG. 1. In some embodiments, the raw plant matter feedstock derived from the fruit and/or seed of the energy crop, such as a corn kernel in a preferred embodiment, is dry milled or wet milled 10 into a milled plant matter feedstock, i.e., flour. Thereafter, the dry or wet milled plant matter feedstock is combined with aqueous liquid and, optionally, an acid to form an acidic aqueous medium 20 (i.e., mash). The liquid may be water, recycled whole stillage, a recycled whole stillage condensate, recycled thin stillage, a recycled thin stillage condensate, or combinations thereof. Acidic adjustment is optional and may be performed in order to adjust the pH of the aqueous medium to the desired acidic pH. In some embodiments of the present invention, the acidic aqueous mixture, i.e., mash, is formed by combining a milled plant matter feedstock, i.e., flour from the milling process, water, and recycled whole stillage. In some embodiments of the present invention, the acidic aqueous medium, i.e., mash, is formed by combining a milled plant matter feedstock, i.e., flour from the milling process, water, recycled whole stillage, and recycled thin stillage. The mash is then cooked 30 by heating the fluid mixture using, for example, steam injection. Heating pastes the starch by breaking up starch crystals and hydrating the starch granules (i.e., gelatinization), which promotes acid hydrolysis of at least a portion of the starch, the cellulose, and/or the hemicellulose into simpler sugars, i.e., oligomers, C6 and C5 monosaccharides, disaccharides, trisaccharides, etc. Acid hydrolysis also separates lignin from lignin-cellulose and lignin hemicellulose complexes. The cooked mash is then cooled and combined with an α-amylase enzyme 40 to form a liquefied medium, wherein the α-amylase enzyme catalyzes enzymatic hydrolysis of at least a portion of the starch to form simple sugars, such as glucose, maltose, maltotriose, limit dextrins, etc.

In some embodiments, at least a portion of the liquefied medium is cooled 50 to prepare it for ethanol fermentation 80, wherein glucoamylase, yeast, and additional nutrients are added to the liquefied medium to form a primary fermentation mixture. Liquefaction typically occurs at elevated temperatures. Therefore, in those embodiments wherein the liquefied medium is prepared for fermentation, the liquefied medium is cooled 50 and glucoamylase, yeast, and additional nutrients are added to the liquefied medium to form a primary fermentation mixture. The action of the yeast converts simple C6 sugars (i.e., glucose) into carbon dioxide and ethanol. In one aspect, at least a portion of the cooled liquefied medium is mixed with glucoamylase, yeast, and additional nutrients to form a propagation mixture. The propagation mixture is aerated so that the action of the yeast converts simple C6 sugars to form additional yeast. In this aspect, at least a portion of the aerated propagation mixture comprising yeast, glucoamylase, and nutrients is added to the liquefied medium, preferably with additional glucoamylase and additional nutrients to form the primary fermentation mixture. In one aspect, propagation is conducted in separate, dedicated equipment from equipment used for fermentation 80.

In some embodiments, propagation or fermentation 80 or both are performed batch-wise in stirred vessels, comprising the sequence of feeding the liquefied medium, glucoamylase, yeast, and additional nutrients to a vessel, holding and stirring the contents of the vessel for a duration following the completion of such additions, and removing at least a portion of the contents of the vessel following the duration of stirring. Optionally, stirring may be performed during the addition step and during the removal step. Optionally, the first two steps may be repeated in sequence prior to the final step. In one aspect, the addition step is performed by continuously adding at least a portion of the glucoamylase and the cooled liquefied medium to the vessel in a substantially fixed ratio. In one aspect, at least a portion of the glucoamylase and the cooled liquefied medium are mixed in the substantially fixed ratio prior to being added to the vessel.

In some embodiments, at least a portion of the liquefied medium is cooled 50 to prepare it for pre-conversion 60 by combining the liquefied medium with an enzyme such as a protease, cellulase, hemicellulase, and the like. Liquefaction typically occurs at elevated temperatures. Therefore, in those embodiments wherein the liquefied medium is subjected to pre-conversion, the liquefied medium is cooled 50 and additional enzymes are added in primary pre-conversion step 60. The enzymatic hydrolysate herein may comprise a variety of enzymes, including but not limited to proteases, xylanases, cellulases, hemicellulases, and combinations of enzymes, which catalyze the enzymatic hydrolysis of xylans, cellulose, and hemicellulose to produce simpler sugars, such as oligomers, C5 and C6 sugars, disaccharides, trisaccharides, etc.

In some embodiments, the enzymatic hydrolysate or liquefied medium is then cooled 70 to prepare it for ethanol fermentation 80, wherein glucoamylase, yeast, and additional nutrients are added to the enzymatic hydrolysate to form a primary fermentation mixture. The action of the yeast converts simple C6 sugars (i.e., glucose) into carbon dioxide and ethanol.

The primary fermentation medium is then routed into a beer still 90, wherein the primary fermentation medium is distilled to carry a portion of the liquid, the high wines, to a rectifier 100. The distilled high wines may then be dehydrated 110, yielding ethanol suitable for use as fuel or for consumption. The material remaining in the beer still after distillation comprises whole stillage.

In some embodiments, at least a portion of the whole stillage feed co-product, is recycled by mixing the whole stillage with dry milled or wet milled plant matter feedstock and water, forming the mash 20, which is then cooked 30, liquefied 40, optionally pre-converted 60, and fermented 60. In some embodiments, the whole stillage is processed to separate thin stillage from the wet cake (i.e., wet distillers grain), e.g., by centrifugation and further processed into animal feed co-products, e.g., WDG, DDG, CDS, etc. In some embodiments, whole stillage and thin stillage are recycled back into the above-described process in forming the mash 20.

In some embodiments, the whole stillage remaining in the beer still 90 may be further processed to convert a portion of any remaining starch, complex polysaccharides, oligosaccharides, etc. to ethanol to thereby enhance the ethanol yield of the process. Further processing removes at least a portion of the components of little nutritive value, thereby enhancing the nutritional quality of the resultant feed product by concentrating the protein and oil content. It should be noted, in this regard, that further processing may be carried out, for example on a whole stillage co-product obtained after ethanol distillation, and may also be carried out, for example, on subsequent process streams such as a WDG obtained from the centrifugation of the whole stillage or even on other co-products such as thin stillage, DDG, DDGS, and WDGS. Simply stated, a variety of feed co-product streams resulting from primary ethanol fermentation/distillation may be subjected to the process of the present invention.

In some embodiments, at least a portion of the feed co-product, (e.g., whole stillage, thin stillage, condensates thereof, DDG, DDGS, WDG, and WDGS) is subjected to thermochemical treatment 120 by combining the feed co-product with an acid, and then heating the feed co-product to thereby promote acid hydrolysis 130 and gelatinization of any remaining starch, complex polysaccharides, oligosaccharides, etc. to simpler carbohydrates.

After cooling 140, the acid hydrolyzed feed co-product is combined with a pre-conversion enzyme, selected from a variety of enzymes, including but not limited to amylase, xylanase, cellulase, hemicellulase, and combinations of enzymes are possible for secondary pre-conversion 150, wherein the enzyme catalyzes enzymatic hydrolysis of at least a portion of any remaining complex polysaccharides into simple sugars, such as oligomers, C5 and C6 sugars, disaccharides, trisaccharides, etc.

The secondary enzymatic hydrolysate formed thereby is then cooled 160 and combined with glucoamylase and yeast to form a secondary fermentation medium 170, whereby any fermentable sugars produced by acid hydrolysis and secondary pre-conversion are converted by secondary fermentation into ethanol. In one aspect, a propagation mixture comprises at least a portion of the yeast, and glucoamylase added to the secondary enzymatic hydrolysate. Such propagation mixture may optionally be formed from a portion of the cooled liquefied medium or from a portion of the secondary enzymatic hydrolysate. In another aspect, the secondary fermentation mixture is formed by continuously adding at least a portion of the glucoamylase and the cooled liquefied medium. The secondary fermentation medium is subjected to solid-liquid separation, such as by centrifugation or filtration 180. The liquid portion is concentrated by evaporation in, for example, a beer still 190, wherein the liquid portion is distilled to separate any ethanol produced by secondary fermentation. The concentrate exiting the beer still 190 is then dried 200, thereby yielding dry condensed solubles. The solids portion, (i.e., WDG) is also dried into a nutritionally enhanced DDG 210. The DDG and condensed solubles may be combined forming a nutritionally enhanced DDGS feed co-product.

The process of the present invention as generally depicted in FIG. 1 is further described more fully below, including variations on the above-described general process.

The raw feedstock, i.e., plant matter, derived from the energy crop (i.e., the fruits and/or seeds of a crop selected from among true grasses, tubers, flowering plants, etc.) for use in the process of the present invention may be dry milled or wet milled to a very fine particle size.

In a dry milling operation, the raw plant matter (i.e., the seed and/or fruit of the energy crop), for example, the entire corn kernel, is first ground, typically using a hammer mill and screens, into flour, which is referred to in the industry as "meal" and processed without separating out the various component parts of the grain. The industry has preferred milling to a relatively course grain since it is thought that cooking is sufficient to paste the starch and a courser grain yields a whole stillage product that is easier to separate into thin stillage and the wet cake. The present inventors have discovered that finely milled flour enhances the overall conversion of starch into ethanol and is not detrimental to the separation of thin stillage from the wet cake. In some embodiments, the grain is dry milled into a flour or meal having particle sizes ranging from about 250 micrometers to about 1200 micrometers, preferably ranging from about 500 micrometers to 750 micrometers. As stated above, after dry milling, the flour comprises all of the grain components, including the protein, starch, fibers, and oil.

In wet milling, the grain is first soaked or steeped in sulfurous acid to soften the grains and allow wet grinding to release the oil-containing germ and coarse fiber from the endosperm. The fiber and germ are separated and the endosperm further processed and separated into starch and protein fractions in some wet milling applications. The separated starch streams from a wet-mill can advantageously serve as a feedstock to the ethanol fermentation process due to the reduced amount of non-fermentable matter entering the process and the ability to capture the oil, protein, and fiber separately which have economic value for human food and other applications. See, McFate, U.S. Pat. No. 3,236,740. Wet milling is preferably done to a fine grind in order to enhance the separation of protein from starch in B grains in the cooking step.

The raw plant matter feedstock for the next step of the process is the flour or meal resulting from dry or wet milling. In some preferred embodiments, the raw plant matter feedstock is finely milled flour from dry milling. In the next step according to the process of a present invention, the meal is formed into an aqueous mixture, i.e., a mash, by slurrying the dry milled or wet milled meal with an aqueous liquid. The liquid used to form the fluid mixture may be water, whole stillage, thin stillage, condensates of whole stillage, condensates of thin stillage, or combinations thereof, the whole stillage, thin stillage, condensates of whole stillage, condensates of thin stillage being feed co-products derived from the ethanol fermentation of plant matter in a prior ethanol fermentation process.

In some embodiments, the mash is formed by mixing milled plant matter feedstock, water, and whole stillage. Whole stillage may comprise between about 8% and about 20% dry matter by weight, more typically between about 9.5% and about 14% dry matter by weight, more typically between about 12% and about 14% dry matter by weight. The whole stillage is a feed co-product derived from the ethanol fermentation of the grain of an energy crop, such that, in some embodiments, whole stillage from a prior batch is actually recycled back into the process of the present invention. Whole stillage comprises a portion of residual starch that was, for one reason or another, not fermented by yeast into alcohol. By using whole stillage backset to prepare the mash for acid hydrolysis, jet cooking, and fermentation, the process of the present invention enhances the conversion of starch into alcohol, thereby improving ethanol yield per a given mass of plant feedstock.

The process of the invention may also be a continuous process, in which process down streams (e.g., whole stillage, thin stillage, condensates of whole stillage and/or condensates of thin stillage) are continuously recycled into the mash.

In some embodiments, the mash is formed by mixing flour, water, whole stillage, and thin stillage. Thin stillage is a feed co-product obtained by the separating coarse solids (i.e., the wet distillers grains, which contains between about 25% dry matter by weight and about 35% dry matter by weight) from the aqueous portion of whole stillage by, for example, centrifugation. Thin stillage typically comprises about 5% dry matter (solubles) by weight. Condensates of whole stillage may also be recycled into the process at this stage, including modified wet distillers grains plus solubles having about 50% dry matter by weight and wet distillers grains plus solubles having about 25 to 35% dry matter by weight. Condensates of thin stillage known as condensed distillers solubles having from 23 to 45% dry matter by weight may also be recycled into the process at this step. Finally, even dried distillers grains or dried distillers grains plus solubles may be recycled to form the mash in the process of the present invention.

The relative proportions of the components of the mash, i.e., dry milled or wet milled feedstock, water, and, optionally, recycled whole stillage, thin stillage, condensates of whole stillage, or condensates of thin stillage are selected such that the mash preferably comprises between about 15% dry matter by weight and about 45% dry matter by weight, more preferably between about 20% dry matter by weight and about 40% dry matter by weight, more preferably between about 30% dry matter by weight and about 37% dry matter by weight. In some embodiments, the mash comprises about 32% dry matter by weight. In some embodiments, the mash comprises about 33% dry matter by weight. In some embodiments, the mash comprises about 34% dry matter by weight. In some embodiments, the mash comprises about 35% dry matter by weight. In some embodiments, it has been discovered that lower amounts of dry matter result in high ethanol yields, such as between about 15% dry matter by weight and about 25% dry matter by weight, such as about 17% dry matter by weight, about 18% dry matter by weight, about 19% dry matter by weight, about 20% dry matter by weight, or about 21% dry matter by weight.

In some embodiments, the mash comprises flour, whole stillage recycle, and water. The mash may be formulated to comprise between about 25 pounds and about 45 pounds of flour per 100 pounds of mash, preferably between about 30 pounds and about 39 pounds of flour per 100 pounds of mash. In International Standard units (metric), the mash may be formulated to comprise between about 25 kilograms and about 45 kilograms of flour per 100 kilograms of mash, preferably between about 30 kilograms and about 39 kilograms of flour per 100 kilograms of mash. The mash may comprise between about 5 pounds and about 50 pounds of whole stillage per 100 pounds of mash, preferably between about 10 pounds and about 40 pounds of whole stillage per 100 pounds of mash. In International Standard units (metric), the mash may comprise between about 5 kilograms and about 50 kilograms of whole stillage per 100 kilograms of mash, preferably between about 10 kilograms and about 40 kilograms of whole stillage per 100 kilograms of mash. The mash may comprise between about 30 pounds and about 70 pounds of water per 100 pounds of mash, preferably between about 35 pounds and about 55 pounds of water per 100 pounds of mash. In International Standard units (metric), the mash may comprise between about 30 kilograms and about 70 kilograms of water per 100 kilograms of mash, preferably between about 35 kilograms and about 55 kilograms of water per 100 kilograms of mash.

In some embodiments, the mash may be formulated with flour, whole stillage recycle, thin stillage recycle, and water. The mash may comprise between about 20 pounds and about 50 pounds of flour per 100 pounds of mash, preferably between about 30 pounds and about 45 pounds of flour per 100 pounds of mash. In International Standard units (metric), the mash may comprise between about 20 kilograms and about 50 kilograms of flour per 100 kilograms of mash, preferably between about 30 kilograms and about 45 kilograms of flour per 100 kilograms of mash. The mash may comprise between about 0 pounds and about 50 pounds of whole stillage per 100 pounds of mash, preferably between about 10 pounds and about 35 pounds of whole stillage per 100 pounds of mash. In International Standard units (metric), the mash may comprise between about 0 kilograms and about 50 kilograms of whole stillage per 100 kilograms of mash, preferably between about 10 kilograms and about 35 kilograms of whole stillage per 100 kilograms of mash. The mash may comprise between about 0 pounds and about 20 pounds of thin stillage per 100 pounds of mash, preferably between about 0 pounds and about 10 pounds of thin stillage per 100 pounds of mash. In International Standard units (metric), the mash may comprise between about 0 kilograms and about 20 kilograms of thin stillage per 100 kilograms of mash, preferably between about 0 kilograms and about 10 kilograms of thin stillage per 100 kilograms of mash. The mash may comprise between about 30 pounds and about 65 pounds of water per 100 pounds of mash, preferably between about 35 pounds and about 60 pounds of water per 100 pounds of mash. In International Standard units (metric), the mash may comprise between about 30 kilograms and about 65 kilograms of water per 100 kilograms of mash, preferably between about 35 kilograms and about 60 kilograms of water per 100 kilograms of mash.

The mash is typically agitated, such as by paddle stirring, stir plate, vortex, or shaker, with heating, typically to a temperature below the gelation point of starch, such as between about 45° C. and about 65° C.

In the next step of the process according to the present invention, the aqueous medium comprising plant matter containing complex polysaccharides including starch, cellulose, and hemicellulose is subjected to acid hydrolysis under generally mild conditions of pH and temperature. To prepare the mash for acid hydrolysis, the pH of the mash may be adjusted to between about 2 and about 6, preferably between about 2 and about 5.5, for example between about 2 and about 4, or at pH such as about 2.5, 4, or 5. In some embodiments, the mash may already have a desirable pH within the range of 2 to 6. For acidic pH adjustment, if necessary, sulfuric acid and hydrochloric acid are typically used since they are inexpensive, but organic acids, such as acetic acid, lactic acid, citric acid, tartaric acid and the like may be used. If necessary, for alkaline pH adjustment, ammonia is generally used, but other bases, such as sodium hydroxide and potassium hydroxide, are applicable. Some bases are preferably avoided, such as calcium hydroxide since there is a risk that calcium may cause some materials to precipitate. Acid hydrolysis initially occurs at a temperature below about 65° C., but more preferably below about 55° C., which is about the gelation point of starch, and may occur at room temperature, preferably above about 45° C. The liquid mash may be agitated by conventional means, such as by paddle stirring, stir plate, vortex, or shaker. Acid hydrolysis may occur under these mild conditions for duration between about five minutes and about 120 minutes.

After a period of mild acidic hydrolysis, the temperature of the aqueous medium may be elevated with indirect heat or more typically, jet cooked with direct steam injection using, for example, a commercial Hydroheater®. The temperature and pressure and shear gelatinizes or 'pastes' the starch (i.e., swells the starch granules with water to hydrate the amylase and amylopectin chains) and render it amenable to enzymatic attack. Jet cooking may further hydrolyze the starch chains. Jet cooking may occur at a temperature of at least about 85° C., or at least about 100° C., such as between about 100° C. and about 200° C., preferably between about 120° C. to 160° C., such as between about 140° C. to 160° C. Direct steam injection disperses the aqueous mixture into mist. To disperse the aqueous mixture into mist, the aqueous medium is preferably pumped into the jet cooker at a pressure of at least about 300 kPa (about 45 psi), preferably at least 350 kPa (about 50 psi), more preferably at least 400 kPa (about 58 psi), even more preferably at least about 410 kPa (about 60 psi), and forced through a jet of high velocity steam introduced into the jet cooker at a pressure of at least 800 kPa (about 115 psi), at least 900 kPa (about 130 psi), at least about 1000 kPa (about 145 psi), at least about 1025 kPa (about 148 psi), or at least about 1035 kPa (about 150 psi). The jet cooker preferably has a back pressure of at least about 25 kPa (about 4 psi), at least about 40 kPa (about 6 psi), or even at least about 50 kPa (about 7 psi) or 75 kPa (about 10 psi), as needed, to prevent flashing. In the jet cooker, the pressure of the aqueous mixture drops by between about 200 kPa (about 30 psi) and about 325 kPa (about 50 psi), such as between about 250 kPa (about 35 psi) and about 300 kPa (about 45 psi), such as about 275 kPa (about 40 psi). The pressure of the steam drops by at least about 700 kPa (about 100 psi), preferably at least about 800 kPa (about 115 psi), such as at least about 850 kPa (about 125 psi), or about 900 kPa (about 130 psi). The pressure drop of the steam and the liquid mixture assists in dispersing the fluid mixture into a mist in the jet cooker. The steam swells starch granules, thereby hydrating the granules and destroying their crystalline structure. Jet cooking at elevated temperature may occur for between about 5 minutes and about 20 minutes, preferably about 10 minutes. Typically, the dextrose equivalency (DE) of the medium resulting from jet cooking and acid hydrolysis is between about 1 and about 12.

Jet cooking under acidic conditions solubilizes and gelatinizes the amylose and branched amylopectin chains of the starch and makes them available for further enzymatic hydrolysis. Moreover, jet cooking thins the material at the temperature at which the material is introduced into the enzymatic reactor. The acidic conditions also hydrolyze at least a portion of the amylose and amylopectin, yielding glucose oligomers. The acidic conditions also serve to condition the cell walls and further enhance the release and availability of the starch. In addition, the acidic condition and temperature in the cooking step breaks down lignin-hemicellulose complexes and may hydrolyze the hemicellulose, thereby producing soluble oligomers and monomers of xylose and arabinose and other sugars. The C5 sugars such as xylose and arabinose comprise the majority of the sugars released and are not readily converted by yeast to alcohol.

In the next step of the process according to the present invention, a thermally stable α-amylase enzyme is added to the aqueous medium comprising gelatinized starch to liquefy it. α-amylase enzyme is available commercially, such as from Novozymes, Liquozyme, CDS, Genencor, among other sources. The gelatinization of the prior step solubilizes starches and, to some extent, breaks the starch components down into lower molecular weight oligomers.

Prior to inoculation of the aqueous medium comprising gelatinized starch with the thermally stable α-amylase enzyme, the mixture is cooled to a temperature between about 70° C. and about 90° C., preferably about 85° C., which is an optimal temperature for the α-amylase enzyme catalyzed hydrolysis reaction. The gelatinized medium may optionally be flashed cooled to the desired temperature. If necessary, the pH of the gelatinized medium is adjusted to between about 4 and about 6.5, preferably between about 4.5 and about 6.5, more preferably between about 5 and about 6.5, such as about 5.8. Typically, the pH is adjusted using ammonia, but other bases may be used, such as sodium hydroxide and potassium hydroxide. Some bases are preferably avoided, such as calcium hydroxide since there is a risk that calcium may cause some materials to precipitate. For acidic pH adjustment, if necessary, sulfuric acid and hydrochloric acid are typically used since they are inexpensive, but organic acids, such as acetic acid, lactic acid, citric acid, tartaric acid and the like may be used.

To initiate liquefaction, the gelatinized medium is inoculated with α-amylase typically to a concentration between about 0.02% and about 0.15% based on the dry weight of the solids, preferably between about 0.04% and about 0.07%, based on the dry weight of the solids. α-amylase inoculation may occur by batchwise or continuous addition. The gelatinized medium may be inoculated in a vessel that may be a holding tank for batchwise addition. The vessel may be a stretch of pipe that allows plug-flow of the medium during continuous α-amylase inoculation. The relative rates of flow of α-amylase and mash are controlled so that the composition in the mixture is maintained within the preferred range of initial conditions. The enzyme inoculate is allowed to liquefy the mixture for a duration typically between about one and about four hours, preferably about three hours, which is generally sufficient to achieve a dextrose equivalence (DE) in the range of about 10 to about 30, such as about 10 to about 20, more typically between about 12 to about 15.

α-Amylase hydrolyzes the starch chains solubilized by acid hydrolysis and cooking to short non-retrograding versions and lowers the viscosity of the liquefied medium. Retrogradation is recrystallization that occurs during cooling, which makes starch resistant to fermentation. α-Amylase acts at random locations along the starch chain and breaks down long-chain carbohydrates, ultimately yielding non-retrograding sugars, such as maltotriose and maltose from amylose (reduction of amylose can be measured using iodine staining), or maltose, glucose, maltodextrins, "limit dextrin" (low MW carbohydrates containing the $\alpha(1\rightarrow 6)$ linkages, which are not hydrolyzed by α-amylase) from amylopectin.

In some embodiments, portions of the liquefied medium may be subjected to simultaneous saccharification and fermentation as further described below. In some embodiments, portions of the liquefied medium may be subjected to yeast propagation as further described below. In some embodiments of the invention, the liquefied medium may be subjected to pre-conversion by inoculating the liquefied medium with a pre-conversion enzyme such as protease, cellulase, hemicellulase, and the like. The post-liquefaction pre-conversion step is carried out for the purpose of converting non-fermentable polysaccharides, such as cellulose, into fermentable sugars, such as glucose, by enzymatically attacking the non-fermentable polysaccharides and breaking the polysaccharides down into simpler sugars.

In those embodiments wherein liquefied medium is subjected to pre-conversion by inoculation with a pre-conversion enzyme, the liquefied medium is preferably cooled to a temperature between about 35° C. and about 55° C. by passage through a heat exchanger or series of heat exchangers. In the pre-conversion step, pre-conversion enzymes are added to the liquefied medium in a primary pre-conversion step. Inoculation of the liquefied medium with pre-conversion enzyme may be batchwise or continuous addition. The liquefied medium may be inoculated in a vessel that may be a holding tank for batchwise addition. The vessel may be a stretch of pipe that allows plug-flow during continuous pre-conversion enzyme inoculation. The relative rates of flow of enzyme and liquefied are controlled so that the composition in the mixture is maintained within the preferred range of initial conditions. The liquefied medium is a low viscosity fluid mixture of maltodextrins having a DE ranging from about 10 to about 30 in which the carbohydrate fraction preferably comprises simple sugars, such as glucose, maltose, maltotriose, and maltodextrin products of acid hydrolysis/enzymatic hydrolysis of starch. Acid hydrolysis and enzymatic hydrolysis of hemicellulose yields xylose, arabinose or low molecular weight oligomers thereof.

In primary pre-conversion, the liquefied medium is inoculated with one or more of a variety of supplemental enzymes, such as proteases, xylanases, cellulases, and hemicellulases.

Primary preconversion typically occurs at a temperature between about 35° C. and about 55° C. Moreover, the pH of the liquefied medium is typically between about 4 and about 6.5, preferably between about 4.5 and about 6.5, more preferably between about 5 and about 6.5, such as about 5.8. The pH is typically also appropriate for primary conversion such that pH adjustment is often unnecessary.

To initiate primary pre-conversion, the liquefied medium is inoculated with one or more of the above-described pre-conversion enzymes to a concentration between about 0.001% and about 0.05% based on the dry weight of the solids. Primary pre-conversion may occur for durations up to about 30 hours, preferably between about 2 hours and about 10 hours.

The various enzymes used to inoculate the liquefied medium catalyze hydrolysis of the oligosaccharides, polysaccharides, and proteins in the medium into simpler organic molecules, e.g., five and six carbon monosaccharides, disaccharides, trisaccharides, amino acids, and short peptide chains.

Proteases are added to hydrolyze peptide bonds that link amino acids together in polypeptide chains. Generally any of the classes of proteases are applicable, e.g., acid, base, or neutral, and proteases are commercially available from, for example, Novozymes and Genencor. In general, fine starch granules, particularly from the endosperm, are encased in a protein matrix. Proteases are useful for hydrolyzing the peptide bonds and releasing these starch granules. Moreover, proteases enhance the solubility of proteins, oligopeptides, and amino acids in the mash. Without being bound by a particular theory, it is thought that hydrolysis of the proteins into peptides and amino acids enhances the nutritional value of the final feed co-product, since peptides and amino acids are relatively more soluble than proteins and thus may be more bioavailable in the feed co-product. A commercially available protease that may be used in the process of the present invention is FermGen™, which is an alkaline protease available from Genencor International. Also useful is Alcalase®, which is an acid protease available from Novozymes Corporation.

Cellulases are a class of enzymes produced chiefly by fungi, bacteria, and protozoans that catalyze the cellulolysis (hydrolysis) of cellulose into glucose, cellobiose, cellotriose, cellotetrose, cellopentose, cellohexose, and longer chain cellodextrins. Cellulases are commercially available from such suppliers as Novozymes and Genencor. Combinations of the five basic types of cellulases may be employed. For example, endo-cellulases may be added to disrupt the crystalline structure of cellulose and expose individual cellulose chains. Exo-cellulase may be added to cleave two units (cellobiose), three units (cellotriose), or four units (cellotetrose) from the exposed chains, while beta-glucosidase may be added to hydrolyse these products into glucose, which is available for fermentation. A commercially available cellulase is GC-220, available from Genencor International.

Hemicellulases may be added to further hydrolyze the various types of hemicelloses and to further breakdown the products of acid hydrolysis. Hemicellulases are commercially available from such suppliers as Novozymes and Genencor.

Xylanases are a class of enzymes which degrade the linear polysaccharide β-1,4-xylan into xylose (a monosaccharide containing five carbon atoms and including an aldehyde functional group). Xylanases are commercially available from such suppliers as Novozymes and Genencor.

Other enzymes may be added to the mash during primary pre-conversion, such as arabinoxylanases and pullulanases. Arabinoxylanases catalyze the hydrolysis of arabinoxylans, yielding arabinose and xylose. Pullulanases are a class of glucanases that catalyze the hydrolysis of amylopectin at the 1-6 bond, thereby yielding oligomers of D-glucose. A commercially available pullulanase is Promozyme® D2, available from Novozyme Corporation. Also useful are multi-enzyme complexes containing multiple carbohydrates, such as Viscozyme® L, available from Novozyme Corporation, which contains arabanase, cellulase, β-glycanase, hemicellulase, and xylanase.

The pre-conversion enzymes catalyze hydrolysis of at least a portion of complex carbohydrates and proteins into simpler molecules, the exact composition of the hydrolysate depending upon the identities of the supplemental enzymes added in to the primary pre-conversion step. The enzymatic hydrolysate is next inoculated with yeast and, optionally, a glucoamylase, to simultaneously cleave any remaining glycosidic linkages and for primary ethanol fermentation.

In some embodiments, a portion of the liquefied medium is subjected to saccharification and fermentation. In some embodiments, portion of the liquefied medium is subjected to simultaneous saccharification and fermentation. Therein, glucoamylase and yeast addition may occur simultaneously, in batch or continuous addition. In some embodiments, saccharification of the liquefied medium occurs to some extent prior to fermentation. In these embodiments, a portion or even all of the glucoamylase is added to the liquefied medium prior to the addition of yeast. Glucoamylase addition may occur batchwise or continuously. Addition of the glucoamylase to the liquefied medium prior to addition of yeast thereby forms a saccharification medium.

In some embodiments, a primary enzymatic hydrolysate is subjected to saccharification and fermentation. In some embodiments, a primary enzymatic hydrolysate is subjected to simultaneous saccharification and fermentation. Therein, glucoamylase and yeast addition may occur simultaneously, in batch or continuous addition. In some embodiments, saccharification of the primary enzymatic hydrolysate occurs to some extent prior to fermentation. In these embodiments, a portion or even all of the glucoamylase is added to the primary enzymatic hydrolysate prior to the addition of yeast. Glucoamylase addition may occur batchwise or continuously. Addition of the glucoamylase to the primary enzymatic hydrolysate prior to addition of yeast thereby forms a saccharification mixture.

To prepare liquefied medium or primary enzymatic hydrolysate for saccharification and ethanol fermentation, the temperature of the liquefied medium or enzymatic hydrolysate may be adjusted to between about 25° C. and about 35° C., preferably about 32° C. Moreover, the pH is preferably adjusted to between about 4.2 and about 4.8, preferably about 4.5. pH adjustment may occur batchwise or continuously by addition of acid or base to the vessel. The vessel may be a holding tank or a stretch of pipe allowing plug flow of the liquefied medium. For acidic pH adjustment, if necessary, sulfuric acid and hydrochloric acid are typically used since they are inexpensive, but organic acids, such as acetic acid, lactic acid, citric acid, tartaric acid and the like may be used. If necessary, for alkaline pH adjustment, ammonia is generally used, but other bases, such as sodium hydroxide and potassium hydroxide, are applicable. Some bases are preferably avoided, such as calcium hydroxide since there is a risk that calcium may cause some materials to precipitate.

Next, the liquefied medium or enzymatic hydrolysate is inoculated with glucoamylase (alternatively, γ-Amylase; Glucan 1,4-α-glucosidase; amyloglucosidase; Exo-1,4-α-glucosidase; glucoamylase; lysosomal α-glucosidase; 1,4-α-D-glucan glucohydrolase) and yeast. Inoculation of the glucoamylase and the yeast may occur by continuous or batchwise addition. The liquefied medium may be inoculated in a vessel that may be a holding tank for batchwise addition. The vessel may be a stretch of pipe that allows plug-flow during continuous glucoamylase inoculation. The relative rates of flow of glucoamylase and liquefied medium or primary enzymatic hydrolysate are controlled so that the composition in the mixture is maintained within the preferred range of initial conditions. In addition to cleaving the last α(1→4) glycosidic linkages at the nonreducing end of amylose and amylopectin, yielding glucose, γ-amylase will cleave α(1→6) glycosidic linkages. The liquefied medium or enzymatic hydrolysate may be inoculated with glucoamylase to a concentration of between about 0.02% and about 0.15%, more preferably between about 0.05% and about 0.08%, based on the dry weight of the solids. Inoculation with glucoamylase thereby forms a saccharification mixture. Glucoamylases are available commercially, such as from Novozyme.

The yeast converts glucose and other 6 carbon sugars to ethanol and carbon dioxide. Inoculation with yeast thereby forms a fermentation mixture. Conventionally, the yeast species is *S. cerevisiae*, but other yeasts that are typically used in fermentation may be used, such as *Saccharomyces carlsbergensis*. The liquefied medium or enzymatic hydrolysate may be inoculated with yeast to a concentration of between about $120 \times 10^6$ cells/mL and about $1 \times 10^9$ cells/mL.

Preferably, at least a portion of glucoamylase is mixed with at least a portion the liquefied medium or enzymatic hydrolysate within the concentration ranges above prior to mixing with yeast. In batch propagation or fermentation processes, described in detail below, such prior mixing is believed to expose the yeast to a consistent initial concentration of simple sugars, neither starving the yeast with a low initial concentration nor inhibiting the yeast with a high initial concentration. More preferably, substantially all the glucoamylase and liquefied medium or enzymatic hydrolysate are mixed within the concentration ranges above prior to the addition of yeast. Most preferably, substantially all the glucoamylase and liquefied medium or enzymatic hydrolysate are mixed within the concentration ranges above immediately prior to adding such mixture to a fermentation or yeast propagation vessel containing yeast or to which yeast is concurrently or later added.

Preferably, the yeast is adapted to the primary fermentation mixture prior to fermentation to ethanol by propagating yeast in at least a portion of the liquefied medium. Propagation is typically performed by forming a propagation mixture comprising yeast, liquefied medium or enzymatic hydrolysate, glucoamylase, and additional nutrients. The propagation mixture is then aerated. In aerobic conditions, the yeast preferentially converts glucose and other 6 carbon sugars to form more yeast. It is believed that such yeast progeny are more efficient at converting 6 carbon sugars to ethanol in a saccharification and ethanol fermentation process performed on the primary fermentation mixture. For batch propagation, propagation is performed for about 15 hours once all ingredients are added to the propagation vessel, after which time the contents of the propagation vessel are preferably transferred to a fermentation vessel. For the reasons stated above, a batch propagation process preferably comprises mixing glucoamylase with at least a portion of the liquefied medium or enzymatic hydrolysate within the glucoamylase concentration ranges described above prior to mixing with yeast to form the propagation mixture.

To enhance the efficacy of saccharification and primary ethanol fermentation and increase the ethanol yield, additional nutrients may be added to enhance yeast proliferation, such as urea, ammonia, free-amino-nitrogen (FAN), oxygen, phosphate, sulfate, magnesium, zinc, calcium, and vitamins such as inositol, pantothenic acid, and biotin. Preferably, urea may be added to a concentration between about 0 and about 32 mmole/liter, preferably between about 8 and about 16 mmole/Liter.

Saccharification and primary ethanol fermentation may occur for between about 45 hours and about 75 hours, preferably for about 60 hours. For batch fermentation, preferably a propagation mixture comprising adapted yeast is initially charged to a fermentation vessel. Typically, such initial charge comprises about 2% to about 5% of the initial primary fermentation mixture volume. At the end of the primary fermentation, the alcohol content in the beer may range from about 10 to about 15% by weight as is basis, typically from 12 to about 15% by weight as is basis, as measured by high performance liquid chromatograph (HPLC) and corrected for suspended solids in the beer.

After primary ethanol fermentation, the resulting product is a beer containing ethanol and whole stillage. The contents of the beer in approximate concentrations is as follows:
Ethanol: 10.0-15.0% by weight as-is
Total solids: 9.5-14.0% by weight as-is
Water: Balance The ethanol is isolated from the beer by conventional means, such as distillation, which separates the high wines (a mixture of ethanol and other liquids, such as water) from the whole stillage. Distillation may be by conventional methods, such as in a beer still, which distills high wines from beer. The whole stillage passes out of the beer still at a temperature of about 105° C.

The high wines are rectified according to conventional methods and dehydrated to produce anhydrous ethanol for use as fuel or potable ethanol.

Whole stillage may comprise between about 8% and about 20% dry matter by weight, typically between about 12% and about 14% dry matter by weight. The whole stillage typically comprises a significant residual starch fraction that did not, for one reason or another, become fermented into ethanol. For example, some free starch granules are not pasted and thus are not available for hydrolysis by acidic conditions or enzymatic catalysis. In some instances, starch granules are wrapped in a protein matrix and are thus not available. Enzymatic hydrolysis is not 100% efficient such that some solubilized dextrins are not hydrolyzed and are therefore not available for fermentation.

While primary ethanol fermentation may convert between about 90% and about 97%, more typically between about 90% and about 95% of the starch portion of the grain into fermentable sugars, this means that between about 3% and about 10%, typically about 5% and about 10% of the starch portion remains in the whole stillage. Moreover, the whole stillage comprises a significant portion of cellulose and hemicellulose. Typically, between about 12% and about 15% of the dry matter by weight in whole stillage is cellulose, while between about 17% and about 26% of the dry matter by weight in whole stillage is hemicellulose. The remainder starch, cellulose, and hemicellulose in the whole stillage may be further processed into fermentable sugars, thereby improving the overall ethanol yield of fermentation.

The components and relative proportions of the total solids, i.e., dry matter, in a whole stillage feed co-product are generally as follows:
Starch and sugars: 3.6-10.0% dry matter basis
Crude protein: 29.0-33.0% dry matter basis
Acid detergent fiber (ADF): 12.0-15.0% dry matter basis
Neutral detergent fiber (NDF): 32.0-38.0% dry matter basis
Crude Fat: 10.6-12.5% dry matter basis
Acid detergent fiber (ADF) generally encompasses cellulose and lignin. Neutral detergent fiber (NDF) generally encompasses cellulose, lignin, and hemicellulose. The starch and sugars generally denotes fermentable sugars or sugars comprising primarily glucose polymers that may be hydrolyzed, by acid, alkaline, enzymatic, or otherwise, into fermentable sugars.

According to the method of the present invention, at least a portion of the whole stillage may be subjected to additional processing as described further herein to improve alcohol yield by converting a portion of the remainder starch, cellulose, and hemicellulose into fermentable sugars for secondary fermentation. The modified feed co-product resulting therefrom, having lower fiber content and conversely a higher protein and fat content on a dry basis, is a nutritionally enhanced feed co-product.

In some embodiments, the further processing comprises recycling at least a portion of the whole stillage back into the primary fermentation process by combining at least a portion of whole stillage with a dry milled or wet milled plant feedstock to form a liquid mash, which is then subjected to the primary ethanol fermentation process as described above, including acid hydrolysis, liquefaction, optionally primary pre-conversion, primary saccharification and ethanol fermentation. Typically, between about 10% and about 40%, such as about 10% to about 30% or about 20% to about 40% of the whole stillage is recycled.

In some embodiments, the further processing comprises separating the liquid portion of whole stillage, i.e., the thin stillage, from the wet cake, i.e., the wet distillers grains, and recycling at least a portion of the thin stillage into the primary fermentation process by combining at least a portion the thin stillage with whole stillage and a dry milled or wet milled plant feedstock to form a liquid mash, which is then subjected to the primary ethanol fermentation process as described above, including acid hydrolysis, liquefaction, optionally primary pre-conversion, and saccharification and primary ethanol fermentation.

Thin stillage typically comprises between about 8% and about 12% dry matter. The components and relative proportions of the total solids, i.e., dry matter, in a thin stillage feed co-product are generally as follows:
Starch: 9-16% dry matter basis
Crude protein: 18-24% dry matter basis
Fat: 16-24% dry matter basis
Crude Fiber: 2-4% dry matter basis
Ash: 8-11% dry matter basis
Insoluble solids 0.8%-4.0% dry matter basis Typically, between about 10% and about 40%, such as about 10% to about 30% or about 20% to about 40% of the thin stillage is recycled. The thin stillage may be concentrated by evaporation to yield condensed distillers solubles, which may also be recycled to form the mash.

In yet another embodiment, at least a portion of the whole stillage may be subjected to further secondary processing (i.e., is not recycled to form a liquid mash with fresh dry milled or wet milled material) as described herein according to the following protocol. Typically, not all of the whole stillage or thin stillage is recycled, i.e., between about 60% and about 90% may be subjected to further secondary processing according to the present invention.

In secondary processing, the whole stillage (or other process streams, such as condensed whole stillage, thin stillage, condensed thin stillage, wet distillers grains, condensed distillers solubles, etc. and combinations of the above) is first subjected to a thermochemical pre-treatment. For the sake of simplicity, the secondary process described below is stated to occur using a whole stillage feed co-product, but other process streams from an ethanol fermentation process, i.e., thin stillage, condensed thin stillage, WDG, CDS, etc., may be subjected to secondary processing.

In the first step of secondary processing, the pH and temperature of the whole stillage (or other process stream, i.e., thin stillage, WDG, WDGS, DDG, DDGS, CDS, etc.) is adjusted, if necessary. If necessary, the aqueous content may be adjusted by, for example, adding water or by condensing the process stream, to yield a composition having between about 5% dry matter by weight and about 14% dry matter by weight. The aqueous material is typically agitated, such as by paddle stirring, stir plate, vortex, or shaker. If necessary, the pH is adjusted to between about 2 and about 6, such as between about 2.5 and about 5.0, preferably between about 2.5 and about 4.5, preferably about 4.5. For acidic pH adjustment, if necessary, sulfuric acid and hydrochloric acid are typically used since they are inexpensive, but organic acids, such as acetic acid, lactic acid, citric acid, tartaric acid and the like may be used. If necessary, for alkaline pH adjustment, ammonia is generally used, but other bases, such as sodium hydroxide and potassium hydroxide, are applicable. Some bases are preferably avoided, such as calcium hydroxide since there is a risk that calcium may cause some materials to precipitate.

The whole stillage is heated to a temperature between about 85° C. and about 200° C., preferably between about 85° C. and about 150° C., such as between about 135° C. and about 145° C., and, in some embodiments, at about 143° C. The whole stillage may be held at this temperature for between about 5 minutes and about 20 minutes, preferably about 10 minutes.

Thermochemical pre-treatment under acidic conditions herein pastes any remaining starch and may achieve a dextrose equivalence (DE) in the range of about 1 to about 4, such as about 1 to about 2, yielding low molecular weight carbohydrate products, including low molecular weight oligomers, trisaccharides, disaccharides, and monosaccharide C6 and C5 sugars, and renders them available for enzymate hydrolysis.

The hydrolyzed mixture is then subjected to secondary pre-conversion by adding α-amylase, and, optionally other degradative enzymes to form a secondary enzymatic hydrolysate. Prior to inoculation of the thermo-chemically treated mixture, the mixture is cooled to a temperature between about 70° C. and about 90° C., preferably about 85° C. The mixture may optionally be flashed cooled to the desired temperature. If necessary, the pH of the mixture is adjusted to between about 4 and about 6.5, preferably between about 4.5 and about 6.5, more preferably between about 5 and about 6.5, such as about 5.8. For alkaline pH adjustment, ammonia is generally used, but other bases, such as sodium hydroxide and potassium hydroxide, are applicable. Some bases are preferably avoided, such as calcium hydroxide since there is a risk that calcium may cause some materials to precipitate. For acidic pH adjustment, if necessary, sulfuric acid and hydrochloric acid are typically used since they are inexpensive, but organic acids, such as acetic acid, lactic acid, citric acid, tartaric acid and the like may be used.

Next, the thermochemically treated stillage is inoculated with thermally stable α-amylase and optionally, additional degradative enzymes may be added, such as proteases, xylanases, cellulases, hemicellulases in a secondary pre-conversion process to act on any remaining polymeric and oligomeric material and reduce it to low molecular weight materials. The thermochemically treated stillage may be inoculated with one or more of the above-described enzymes to a concentration between about 0.001% and about 0.05% based on the dry weight of the solids. Inoculation may occur by continuous or batchwise addition. To enhance secondary pre-conversion, nutrients may be added, particularly a source of nitrogen such as urea or ammonia.

Secondary preconversion may occur for between about one and about six hours, preferably between about one and about four hours, more preferably between about two hours and about three hours, such as about three hours. Typically, the secondary preconversion may achieve dextrose equivalence (DE) in the range of about 10 to about 40, such as about 10 to about 30.

To prepare the secondary enzymatic hydrolysate for secondary ethanol fermentation, the temperature of the secondary enzymatic hydrolysate may be adjusted to between about 25° C. and about 35° C., preferably about 32° C. Moreover, the pH is preferably adjusted to between about 4.2 and about 4.8, preferably about 4.5. For acidic pH adjustment, if necessary, sulfuric acid and hydrochloric acid are typically used since they are inexpensive, but organic acids, such as acetic acid, lactic acid, citric acid, tartaric acid and the like may be used. For alkaline pH adjustment, ammonia is generally used, but other bases, such as sodium hydroxide and potassium hydroxide, are applicable. Some bases are preferably avoided, such as calcium hydroxide since there is a risk that calcium may cause some materials to precipitate.

The secondary enzymatic hydrolysate is next inoculated with glucoamylase (alternatively, γ-Amylase; Glucan 1,4-α-glucosidase; amyloglucosidase; Exo-1,4-α-glucosidase; glucoamylase; lysosomal α-glucosidase; 1,4-α-D-glucan glucohydrolase) and yeast for simultaneous saccharification and fermentation. Inoculation with glucoamylase may occur by continuous or batchwise addition. In addition to cleaving the last α(1→4) glycosidic linkages at the nonreducing end of amylose and amylopectin, yielding glucose, γ-amylase will cleave α(1→6) glycosidic linkages. The enzymatic hydrolysate may be inoculated with glucoamylase to a concentration of between about 0.02% and about 0.15%, more preferably between about 0.05% and about 0.08%, based on the dry weight of the solids.

Yeast converts glucose and other 6 carbon sugars to ethanol and carbon dioxide. Conventionally, the yeast species is *S. cerevisiae*, but other yeasts that are typically used in fermentation may be used, such as *Saccharomyces carlsbergensis*. The enzymatic hydrolysate may be inoculated with yeast to a concentration of between about $120 \times 10^6$ cells/mL and about $1 \times 10^9$ cells/mL. Preferably, at least a portion of the yeast has been propagated on secondary fermentation medium, similar to yeast propagation described above for primary fermentation media. To avoid starving and inhibiting yeast during such propagation or secondary fermentation, the secondary enzymatic hydrolysate is preferably inoculated with glucoamylase within the ranges described above prior to mixing with yeast and most preferably prior to addition to a propagation or fermentation vessel.

To enhance the efficacy of saccharification and secondary ethanol fermentation and increase the ethanol yield, additional nutrients may be added, such as urea, ammonia, FAN=free-amino-nitrogen, oxygen, phosphate, sulfate, magnesium, zinc, calcium, and vitamins such as inositol, pantothenic acid, and biotin.

Secondary ethanol fermentation may occur for between about 45 hours and about 75 hours, preferably for about 60 hours. At the end of secondary ethanol fermentation, the ethanol content may range from about 12 to about 15 wt. %, as measured by high performance liquid chromatography (HPLC) and adjusted for insoluble solids content.

Preferably, the solids and liquids in the product of secondary ethanol fermentation are separated by centrifugation or filtration. The liquid portion is routed to a beer still, wherein ethanol is isolated from the secondary beer by conventional means, such as distillation, which separates the high wines (a mixture of ethanol and other liquids, such as water) from the fermented stillage. The high wines are rectified according to conventional methods and dehydrated to produce anhydrous ethanol for use as fuel or potable ethanol. The remaining liquid portion is then condensed by evaporation and dried, yielding dry condensed solubles. The solid portion, i.e., the wet distillers grains, may optionally be drying into dried distillers grains and combined with the dry condensed solubles, yielding dry distillers grains with solubles.

The present invention therefore encompasses several variations designed to enhance the conversion of starch to sugar, to convert non-fermentable polysaccharides into fermentable sugars, and to enhance the ethanol yield.

The embodiments of the present invention as set forth herein further yield a feed co-product of enhanced nutritional quality. In some embodiments, the feed co-product of enhanced nutritional quality comprises a relatively higher proportion of protein compared to feed co-products prepared by conventional fermentation methods. In some embodiments, the process of the present invention substantially reduces the fiber content compared to a conventional process in which grain is subjected to a single fermentation step.

Therefore, the present invention is further directed to a feed co-product of improved nutritional quality. By removing a portion of the fiber, which has little nutritive value, the dry distillers grains with solubles that remains after removal of the ethanol and evaporation/drying has, on a dry basis, enhanced protein and oil content. The resulting feed co-product therefore has an improved nutritional profile.

The process of the present invention produces an improved feed co-product having enhanced protein content and reduced fiber content compared to prior methods. For example, cellulose (C-6 fiber components) and hemicellulose (C-5 fiber components) are generally consumed by the enzymatic treatments herein described, thereby reducing the quantity of these fiber components in the feed co-product.

The enhanced feed co-product produced by the process of the present invention may be characterized by an increase in the total amount of protein compared to whole stillage produced by conventional methods. The process of the present invention yields a protein content improvement of at least 5% by weight on a dry basis compared to the whole stillage product of a conventional fermentation process. More typically, the improvement in protein content is at least about 7% by weight on a dry basis, or even at least 10% by weight on a dry basis. Whole stillage produced by conventional fermentation typically contains about 30% by weight protein on a dry basis. Accordingly, the total protein content of the feed co-product produced by the method of the present invention may be at least about 32% by weight of the feed co-product on a dry basis, typically, at least about 34% by weight of the feed co-product on a dry basis.

In some embodiments, the feed co-product produced by the method of the present invention may be exposed to one or more cellulolytic micro-organism(s) capable of utilizing the fiber component of the feed co-product as a substrate for growth and proliferation, as described in PCT Publication No. WO 2009/079183 (U.S. Prov. App. Ser. No. 61/013,695; U.S. application Ser. No. 12/747,992), the entire disclosure of which is hereby incorporated as if set forth in its entirety. As therein described, cellulolytic micro-organisms are microbes possessing an enzyme or enzyme system that can break down the cellulose and/or hemicellulose to form simple sugar(s), i.e., capable of producing one or more cellulase, hemicellulase, or cellusome complex. The microbe then uses the simple sugar along with other nutrients such as nitrogen and/or phosphorous to grow and proliferate, thereby increasing the microbial protein content of the feed co-product.

The process of the present invention additionally increases ethanol yield compared to conventional process. The ethanol yield may be measured by combining the ethanol resulting from primary fermentation with ethanol resulting from secondary processing and fermentation. Conventional ethanol processes generally yield about 2.6 gallons ethanol per bushel of corn. By comparison, the ethanol yield per bushel of the process of the present invention is typically greater than about 2.8 gallons of ethanol per bushel of corn, more typically between about 2.85 and about 2.9 gallons of ethanol per bushel of corn.

Having described the invention in detail, it will be apparent that modifications and variations are possible without departing from the scope of the invention defined in the appended claims.

EXAMPLES

The following non-limiting examples are provided to further illustrate the present invention.

Example 1

Control Experiment

A control experiment, designated Run #4139, was carried out in which glucoamylase was added in a batch, and the urea was added in two batches. The experimental conditions are as follows:

Corn flour (979 pound/hour; 444 kg/hour) was conveyed into the Mix Tank (1500 gallon capacity; 5678 Liter capacity). The flour was made by grinding #2 yellow dent corn in a Bliss Model EX 1912 TF hammer mill using 0.125 inch (3.175 mm) (38% open area) opening screens. Process water (1440 pound/hour; 653 kg/hour) was added along with thin stillage (197 pound/hour; 89.4 kg/hour) obtained from the adjacent commercial facility as back set. About 12% of the water added was backset. The thin stillage added contained 9.3% total solids by weight and 2.5% insoluble solids by weight on an as-is basis. No whole stillage was added. Mix Tank residence time was 2.7 hours, the temperature was 141° F. (60.6° C.), and the pH was maintained at 4.8 without adjustment. 96% of the total solids on a dry solids basis were provided by the corn flour in the slurry going to the jet heater.

The slurry from the Mix Tank was pumped at a rate of 2771 pounds/hour (1256.9 kg/hour) to the Model M106AS HydroHeater steam-injection jet heater. A minimum flow of 362 pounds/hour (164 kg/hour) of 150 psig (1034 kPa) saturated steam was estimated to have been delivered to the HydroHeater to give a 298° F. (147.8° C.) jet exit temperature to paste the starch. Pressures in the hold coil downstream of the jet were 51 psig (351.6 kPa) at the inlet and 45 psig (310 kPa) at the exit. The flow residence time in the cook tube was about 10 minutes.

The hot mash was flash cooled after it exited the back pressure valve from the hold coil and entered the 300 gallon (1135.6 Liter) vacuum Flash Tank. Ammonium hydroxide (26 Baume) was added to keep the pH at 5.6 and the temperature was maintained at 190° F. (87.8° C.) by vacuum cooling. α-amylase (7.6 mL/min, Novozyme Liquozyme) was added at a 0.0014 wt. enzyme/wt of dry solids dosage.

The enzyme-treated mash was then pumped to the 1100 gallon (4164 Liter) Liquefaction Tank for 100 minutes of nominal hold time at 175° F. (79.4° C.) to further liquefy the pasted starch. The pH averaged about 5.0 in the Liquefaction Hold Tank.

The pH was adjusted to 4.7 after leaving the Liquefaction Tank and the temperature was lowered to 88° F. (31° C.) using plate and frame in-line coolers. Glucoamylase was not added continuously in this trial after the coolers. The total solids were checked and inputs at the Mix tank adjusted to maintain 34% total solids as-is basis going to the Fermentors and Propagation.

The 300 gallon (1135.6 Liter) Propagation Tank was filled to the 250 gallon mark (946.4 Liter) with the cooled mash. The Propagation Tank batch was treated with glucoamylase enzyme (0.625 gallons; 2.366 Liters; Novozyme Spirizyme Fuel) for a 0.00079 pound (0.358 grams) glucoamylase enzyme per pound (0.453 kg) dry solids dosage. Lactrol antibiotic (0.01 pound; 4.54 grams) was added plus Red Star yeast (1 pound; 453.6 grams) per Propagation tank. The Propagation tank was aerated with air (100 standard cubic feet per minute; 2.83 cubic meters per minute). The Propagation tank was pitched to the Fermentor at the 5% Fermentor fill level. Each Propagation Tank took about 50 minutes to fill and was pitched to the following Fermentor after 15 hours of fermentation time.

Four Fermentors (8000 gallon capacity; 30,283 Liters) were filled for 15 hours each. Urea solution (five gallons (18.9 Liters) at a concentration of 32% solids) were added to each fermentor at the 5% fill mark and another 6.3 gallons (23.8 Liters) at the 60% fill mark. Lactrol antibiotic (0.31 pound; 0.14 kg) was added to each fermentor. The fermentation temperature was maintained at 90° F. (32° C.) by cooling jackets with temperature control and the fermentors agitation was maintained. The fermentors were dropped to the beer well after 60 hours of fermentation and the amount of beer determined by totalizing the flows which yielded 38,700 pounds (17554 kg) to 41,800 pounds (18960 kg) of beer.

Each fermentor was analyzed and the empirical data of this Example is presented in the Tables below.

Example 2

Control Experiment

A control experiment, designated Run #4146, was carried out in which glucoamylase was added in a single batch, and urea was added in a single batch. The experimental conditions are as follows:

Corn flour (1202 pounds/hour; 545 kg/hour) was conveyed into the Mix Tank (1500 gallon capacity; 5678 Liter capacity). The flour was made by grinding #2 yellow dent corn in a Bliss Model EX 1912 TF hammer mill using 0.25 inch (6.35 mm) (40% open area) opening screens. Process water (1344 pound/hour; 609 kg/hour) was added along with thin stillage (259 pounds/hour; 117.5 kg/hour) obtained from the adjacent commercial facility as back set. About 16% of the liquid added was backset. The thin stillage added contained 9.6% total solids and 1.5% insoluble solids by weight on an as-is basis. No whole stillage was added. Mix Tank residence time was 2.6 hours, the temperature was 142° F. (61.1° C.), and the pH was maintained at 4.8 without adjustment. 95.5% of the total solids on a dry solids basis were provided by the corn flour in the slurry going to the jet heater.

The slurry from the Mix Tank was pumped at a rate of 2799 pounds/hour (1269.6 kg/hour) to the Model M106AS HydroHeater steam-injection jet heater. A minimum flow of 348 pounds/hour (157.85 kg/hour) of 150 psig (1034 kPa) saturated steam was estimated to have been delivered to the HydroHeater to give a 291° F. (144° C.) jet exit temperature to paste the starch. The mean hold coil temperature was 284° F. (140° C.) in the hold coil downstream of the jet. Pressures were 58.9 psig (406 kPa) at the inlet and 49.9 psig (344 kPa) at the exit. The flow residence time in the cook tube was about 10 minutes.

The hot mash was flash cooled after it exited the back pressure valve from the hold coil and entered the 300 gallon (1135.6 Liter) vacuum Flash Tank. Ammonium hydroxide (26 Baume) was added to keep the pH at 5.75 and the temperature was maintained at 190° F. (87.8° C.) by vacuum cooling. α-amylase (5.3 mL/min; Novozyme Liquozyme) was added at a 0.00081 wt. enzyme/wt of dry solids dosage.

The enzyme-treated mash was then pumped at 6.0 gallons per minute (22.7 Liters per minute) to the 1100 gallon (4164 Liter) Liquefaction Tank for 89 minutes of nominal hold time at 188° F. (86.7° C.) to further liquefy the pasted starch. The pH averaged about 6.0 in the Liquefaction Hold Tank.

The pH was adjusted to 3.5 after leaving the Liquefaction Tank and the temperature was lowered to 88° F. (31° C.) using plate and frame in-line coolers. The total solids were checked and inputs at the Mix tank adjusted to maintain 31.7% total solids as-is basis going to the Fermentors and Propagation.

The 300 gallon (1135.6 Liter) Propagation Tank was filled to the 245 gallon (927 Liter) mark with the cooled mash. Lactrol antibiotic (0.01 pound; 4.54 grams) was added plus Red Star yeast (1 pound; 453.6 grams) per Propagation tank. The Propagation tank was aerated with air (100 standard cubic feet per minute; 2.83 cubic meters per minute). The Propagation tank was pitched to the Fermentor at the 5% Fermentor fill level. Each Propagation Tank took about 45 minutes to fill and was pitched to the following Fermentor after 15 hours of fermentation time.

Four Fermentors (8000 gallon capacity; 30,283 Liters) were filled for 15 hours each. Urea solution (10.53 gallons (39.9 Liters) of 32% solids concentration) was added to each fermentor at the 5% fill mark. Glucoamylase (4901 mL; Novozyme Spirizyme Fuel) enzyme was added to each fermentor at this time as well for a 0.00074 wt. enz./wt. of dry solids dosage. No antibiotic was added to the fermentors. The fermentation temperature was maintained at 88° F. (31° C.) by cooling jackets with temperature control and the fermentors agitation was maintained. The fermentors were dropped to the beer well after 60 hours of fermentation and the amount of beer determined by totalizing the flows which yielded 45,574 pounds (20,672 kg) to 46,881 pounds (21,265 kg) of beer.

Each fermentor was analyzed and the empirical data of this Example is presented in the Tables below.

Example 3

Control Experiment

A control experiment, designated Run #4150, was carried out in which glucoamylase was added continuously. The experimental conditions are as follows:

Corn flour (1060 pounds/hours; 480.8 kg/hour) was conveyed into the Mix Tank (1500 gallon capacity; 5678 Liter capacity). The flour was made by grinding #2 yellow dent corn in a Bliss Model EX 1912 TF hammer mill using 0.25 inch (6.35 mm) (40% open area) opening screens. Process water (1218 pound/hour; 552.5 kg/hour) was added along with thin stillage (257 pounds/hour; 116.6 kg/hour) obtained from the adjacent commercial facility as back set. About 17% of the liquid added was backset. The thin stillage added contained 9.0% total solids and 2.4% insoluble solids by weight on an as-is basis. No whole stillage was added. Mix Tank residence time was 2.5 hours, the temperature was 142° F. (61.1° C.), and the pH was maintained at 5.0 without adjustment. 91.9% of the total solids on a dry solids basis were provided by the corn flour in the slurry going to the jet heater.

The slurry from the Mix Tank was pumped at a rate of 2888 pounds/hour (1310 kg/hour) to the Model M106AS HydroHeater steam-injection jet heater. A minimum flow of 351 pounds/hour (159 kg/hour) of 150 psig (1034 kPa) saturated steam was estimated to have been delivered to the HydroHeater to give a 289° F. (142.8° C.) jet exit temperature to paste the starch. The hold coil exit temperature was not measured in the hold coil downstream of the jet. Pressures were 58.0 psig (400 kPa) at the inlet and 49.0 psig (337.8 kPa) at the exit of the hold coil. The flow residence time in the cook tube was about 10 minutes.

The hot mash was flash cooled after it exited the back pressure valve from the hold coil and entered the 300 gallon (1135.6 Liter) vacuum Flash Tank. The residence time was about 13 minutes. Ammonium hydroxide (26 Baume) was added to keep the pH at 6.2 and the temperature was maintained at 174° F. (78.9° C.) by vacuum cooling. α-amylase (5.0 mL/min, Novozyme Liquozyme) was added at a 0.00077 wt. enzyme/wt of dry solids dosage.

The enzyme-treated mash was then pumped at 6.1 gallons per minute (23.1 Liters per minute) to the 1100 gallon (4164 Liter) Liquefaction Tank for 87 minutes of nominal hold time at 132° F. (55.6° C.) to further liquefy the pasted starch. The pH averaged about 6.2 in the Liquefaction Hold Tank.

The pH was adjusted to 4.8 after leaving the Liquefaction Tank and the temperature was lowered to 88° F. (31.1° C.) using plate and frame in-line coolers. The total solids were checked and inputs at the Mix tank adjusted to maintain 31.4% total solids as-is basis going to the Fermentors and Propagation. Glucoamylase (5 mL/min.; Novozyme Spirizyme Fuel) enzyme was added continuously to the mash going to Propagation and Fermentation at this time for a 0.00073 wt. enz./wt. of dry solids dosage.

The 300 gallon (1135.6 Liter) Propagation Tank was filled to the 245 gallon (927 Liter) mark with the cooled mash. Lactrol antibiotic (0.01 pound; 4.54 grams) was added plus Red Star yeast (1 pound; 453.6 grams) per Propagation tank. The Propagation tank was aerated with air (100 standard cubic feet per minute; 2.83 cubic meters per minute). The Propagation tank was pitched to the Fermentor at the 5% Fermentor fill level. Each Propagation Tank took about 45 minutes to fill and was pitched to the following Fermentor after 15 hours of fermentation time.

Four Fermentors (8000 gallon capacity; 30,283 Liters) were filled for 15 hours each. Urea solution (11 gallons (41.6 Liters) of 32% solids concentration) was added to each fermentor at the 5% fill mark. No antibiotic was added to the fermentors. The fermentation temperature was maintained at 88° F. (31.1° C.) by cooling jackets with temperature control and the fermentors were agitated. The fermentors were dropped to the beer well after 60 hours of fermentation. The amount of beer determined by summing the flow which yielded a range of 52,832 pounds (23,964 kg) to 54,007 pounds (24,497 kg) of beer for the four fermentors.

Each fermentor was analyzed and the empirical data of this Example is presented in the Tables below.

Example 4

Whole Stillage Recycle

A process, designated Run #4209, according to the present invention was carried out in which the mash was prepared with 23% Whole Stillage recycle. The process of this Example is as follows:

Corn flour (1172 pounds/hour; 531.6 kg/hour) was conveyed into the Mix Tank (1500 gallon capacity; 5678 Liter capacity). The flour was made by grinding #2 yellow dent corn in a Bliss Model EX 1912 TF hammer mill using 0.25 inch (6.35 mm) (40% open area) opening screens. Process water (1535 pound/hour; 696.3 kg/hour) was added along with whole stillage (449 pounds/hour; 203.7 kg/hour) obtained from the adjacent commercial facility as back set. About 23% of the liquid added was whole stillage backset. The whole stillage used had 16.2% as-is basis total solids and 11.9% as-is insoluble solids. No thin stillage was added. Mix Tank residence time was 2.6 hours, the temperature was 146° F. (63.3° C.), and the pH was maintained at 5.0 without adjustment.

The slurry from the Mix Tank was pumped at a rate of 2918 pounds/hour (1323.6 kg/hour) to the Model M106AS HydroHeater steam-injection jet heater. A minimum flow of 410 pounds/hour (186 kg/hour) of 150 psig (1034 kPa) saturated steam was estimated to have been delivered to the HydroHeater to give a 300° F. (148.9° C.) jet exit temperature to paste the starch. The hold coil exit temperature was measured at 291° F. (143.9° C.) downstream of the jet. Pressures were 75.5 psig (520.5 kPa) at the inlet and 60.4 psig (416.4 kPa) at the exit of the hold coil. The flow residence time in the cook tube was about 10 minutes.

The hot mash was flash cooled after it exited the back pressure valve from the hold coil and entered the 300 gallon (1135.6 Liter) vacuum Flash Tank. The residence time was about 18 minutes. Ammonium hydroxide (26 Baume) was added to keep the pH at 6.2 and the temperature was maintained at 187° F. (86.1° C.) by vacuum cooling. α-amylase (5.0 mL/min; Novozyme Liquozyme) was added at a 0.00071 wt. enzyme/wt of dry solids dosage.

The enzyme-treated mash was then pumped at 6.0 gallons per minute (22.7 Liters per minute) to the 1100 gallon (4164 Liter) Liquefaction Tank for 89 minutes of nominal hold time at 155° F. (68.3° C.) to further liquefy the pasted starch.

The pH was adjusted to 5.0 using sulfuric acid after leaving the Liquefaction Tank and the temperature was lowered to 89° F. (31.7° C.) using plate and frame in-line coolers. Glucoamylase enzyme (6 mL/min.; Novozyme Spirizyme Fuel) was added continuously to the mash going to Propagation and Fermentation at this time for a 0.00080 wt. enz./wt. of dry solids dosage. The total solids were checked and inputs at the Mix tank adjusted to maintain 33.4% total solids as-is basis going to the Fermentors and Propagation.

The 300 gallon (1135.6 Liter) Propagation Tank was filled to the 245 gallon (927.4 Liter) mark with the cooled mash. Lactrol antibiotic (0.01 pound; 4.54 grams) was added plus Red Star yeast (1 pound; 453.6 grams) per Propagation tank. The Propagation tank was aerated with air (100 standard cubic feet per minute; 2.83 cubic meters per minute). The Propagation tank was pitched to the Fermentor at the 5% Fermentor fill level. Each Propagation Tank took about 45 minutes to fill and was pitched to the following Fermentor after 15 hours of fermentation time. Yeast counts in the Propagation Tank at transfer were: 373 million live, 145 million budding; 46 million dead.

Two 8000 gallon (30,283 Liter) Fermentors were filled for 15 hours each. Urea solution (32% solids; 11 gallons (41.6 Liters)) was added to each fermentor at the 5% fill mark. No antibiotic was added to the fermentors. The fermentation temperature was maintained at 88.5° F. (31.4° C.) by cooling jackets with temperature control and the fermentors were agitated. The fermentors were dropped to the beer well after 60 hours of fermentation and the amount of beer determined by totalizing the flow which yielded a range of 46,315 pounds (21,008 kg) to 47,566 pounds (21,576 kg) of beer for the two fermentors.

Each fermentor was analyzed and the empirical data of this Example is presented in the Tables below.

Example 5

Whole Stillage Recycle

A process, designated Run #4211, according to the present invention was carried out in which the mash was prepared with 45% Whole Stillage. The process of this Example is as follows:

Corn flour (1078 pounds/hour; 488.97 kg/hour) was conveyed into the Mix Tank (1500 gallon capacity; 5678 Liter capacity). The flour was made by grinding #2 yellow dent corn in a Bliss Model EX 1912 TF hammer mill using 0.25 inch (6.35 mm) (40% open area) opening screens. Process water (1309 pound/hour; 593.8 kg/hour) was added along with whole stillage (1062 pounds/hour; 481.7 kg/hour) obtained from the adjacent commercial facility as back set. About 45% of the liquid added was whole stillage backset. The whole stillage used had 16.4% as-is basis total solids and 10.7% as-is insoluble solids. No thin stillage was added. Mix Tank residence time was 2.6 hours, the temperature was 141° F. (60.6° C.), and the pH was maintained at 5.1 without adjustment. 82.8% of the dry solids were estimated to be provided by the corn flour.

The slurry from the Mix Tank was pumped at a rate of 2924 pounds/hour (1326 kg/hour) to the Model M106AS HydroHeater steam-injection jet heater. A steam flow of 468 pounds/hour (212.3 kg/hour) of 150 psig (1034 kPa) saturated steam was measured to the HydroHeater to give a 297° F. (147.2° C.) jet exit temperature to paste the starch. The hold coil exit temperature was measured at 291° F. (143.9° C.) downstream of the jet. Pressures were 72.6 psig (500.6 kPa) at the inlet and 56.5 psig (389.6 kPa) at the exit of the hold coil. The flow residence time in the cook tube was about 10 minutes.

The hot mash was flash cooled after it exited the back pressure valve from the hold coil and entered the 300 gallon (1135.6 Liter) vacuum Flash Tank. The tank residence time was about 20 minutes. Ammonium hydroxide (26 Baume) was added to keep the pH at 6.2 and the temperature was maintained at 188° F. (86.7° C.) by vacuum cooling. α-amylase (5.5 mL/min; Novozyme Liquozyme) was added at a 0.00085 wt. enzyme/wt of dry solids dosage.

The enzyme-treated mash was then pumped at 5.6 gallons per minute (21.2 Liters per minute) to the 1100 gallon (4164 Liter) Liquefaction Tank for 88 minutes of nominal hold time at 168° F. (75.6° C.) to further liquefy the pasted starch.

The pH was adjusted to 4.4 using sulfuric acid after leaving the Liquefaction Tank and the temperature was lowered to 88° F. (31.1° C.) using plate and frame in-line coolers. Glucoamylase enzyme (6.8 mL/min.; Novozyme Spirizyme Fuel) enzyme was added continuously to the mash going to Propagation and Fermentation at this time for a 0.00099 wt. enz./wt. of dry solids dosage. The total solids were checked and inputs at the Mix tank adjusted to maintain 33.2% total solids as-is basis going to the Fermentors and Propagation.

The 300 gallon (1135.6 Liter) Propagation Tank was filled to the 250 gallon (946.4 Liter) mark with the cooled mash. Lactrol antibiotic (0.01 pound; 4.54 grams) was added plus Red Star yeast (1 pound; 453.6 grams) per Propagation tank. The Propagation tank was aerated with air (100 standard cubic feet per minute; 2.83 cubic meters per minute). The Propagation tank was pitched to the Fermentor at the 5% Fermentor fill level. Each Propagation Tank took about 45 minutes to fill and was pitched to the following Fermentor after 15 hours of fermentation time. Yeast counts in the Propagation Tank at transfer were: 283 million live, 156 million budding; 28 million dead.

Two 8000 gallon (30,283 Liter) Fermentors were filled for 15 hours each. Urea solution (32% solids; 11 gallons (41.6 Liters)) was added to each fermentor at the 5% fill mark. No antibiotic was added to the fermentors. The fermentation temperature was maintained at 84.2° F. (29° C.) and 91.8° F. (33.2° C.) by cooling jackets with temperature control and the fermentors were agitated. The fermentors were dropped to the beer well after 60 hours of fermentation and the amount of beer determined by totalizing the flow which yielded a range of 44,579 pounds (20,221 kg) to 44,921 pounds (20,376 kg) of beer for the two fermentors.

Each fermentor was analyzed and the empirical data of this Example is presented in the Tables below.

Example 6

Fine Milling of Corn

A process, designated Run #4255, according to the present invention was carried out in which the mash was prepared with finely milled corn. The process of this Example is as follows:

Corn flour (1188 pounds/hour; 538.9 kg/hour) was conveyed into the Mix Tank (1500 gallon capacity; 5678 Liter capacity). The flour was made by grinding #2 yellow dent corn in a Bliss Model EX 1912 TF hammer mill using 0.125 inch (3.175 mm) (38% open area) opening screens. Process water (1747 pound/hour; 792.4 kg/hour) was added along with thin stillage (349 pounds/hour; 158.3 kg/hour) obtained from the adjacent commercial facility as back set. About 16.6% of the liquid added was thin stillage backset. The thin stillage used had 10.3% as-is basis total solids and 3.7% as-is insoluble solids. No whole stillage was added. Mix Tank residence time was 1.9 hours, the temperature was 145° F. (62.8° C.), and the pH was maintained at 4.8 without adjustment. 95.8% of the dry solids were estimated to be provided by the corn flour.

The slurry from the Mix Tank was pumped at a rate of 3154 pounds/hour (1430.6 kg/hour) to the Model M106AS HydroHeater steam-injection jet heater. A steam flow of 545 pounds/hour (247.2 kg/hour) of 150 psig (1034 kPa) saturated steam was measured to the HydroHeater to give a 292° F. (144.4° C.) jet exit temperature to paste the starch. The hold coil exit temperature was measured at 286° F. (141.1° C.) downstream of the jet. Pressures were 80.4 psig (554.3 kPa) at the inlet and 37.2 psig (256.5 kPa) at the exit of the hold coil. The flow residence time in the cook tube was about 10 minutes.

The hot mash was flash cooled after it exited the back pressure valve from the hold coil and entered the 300 gallon (1135.6 Liter) vacuum Flash Tank. The tank residence time was about 17 minutes. Ammonium hydroxide (26 Baume) was added to keep the pH at 5.2 and the temperature was maintained at 173° F. (78.3° C.) by vacuum cooling. α-amylase (5.0 mL/min; Novozyme Liquozyme) was added at a 0.00067 wt. enzyme/wt of dry solids dosage.

The enzyme-treated mash was then pumped at 5.6 gallons per minute (21.2 Liters per minute) to the 1100 gallon (4164 Liter) Liquefaction Tank for 81 minutes of nominal hold time at 186° F. (85.6° C.) to further liquefy the pasted starch.

The pH was adjusted to 4.2 using sulfuric acid after leaving the Liquefaction Tank and the temperature was lowered to 89° F. (31.7° C.) using plate and frame in-line coolers. Glucoamylase enzyme (6.0 mL/min.; Novozyme Spirizyme Fuel) enzyme was added continuously to the mash going to Propagation and Fermentation at this time for a 0.00076 wt. enz./wt. of dry solids dosage. The total solids were checked and inputs at the Mix tank adjusted to maintain 33.6% total solids as-is basis going to the Fermentors and Propagation.

The 300 gallon (1135.6 Liter) Propagation Tank was filled to the 245 gallon (927.4 Liter) mark with the cooled mash. Lactrol antibiotic (2 grams) was added plus Red Star yeast (1 pound; 453.6 grams) per Propagation tank. The Propagation tank was aerated with air (20 standard cubic feet per minute; 0.57 cubic meters per minute). The Propagation tank was pitched to the Fermentor at the 5% Fermentor fill level. Each Propagation Tank took about 45 minutes to fill and was pitched to the following Fermentor after 15 hours of fermentation time. Yeast counts in the Propagation Tank at transfer were: 420 million live, 171 million budding; 45 million dead.

Three 8000 gallon (30,283 Liter) Fermentors were filled for 15 hours each. Urea solution (32% solids; 11 gallons (41.6 Liters)) was added to each fermentor at the 5% fill mark. No antibiotic was added to the fermentors. The fermentation temperature was maintained at 88.4° F. (31.3° C.) by cooling jackets with temperature control and the fermentors were agitated. The fermentors were dropped to the beer well after 60 hours of fermentation and the amount of beer determined by totalizing the flow which yielded a range of 50,183 pounds (22,763 kg) to 51,060 pounds (23,160 kg) of beer for the two fermentors retained in the yield analysis. The third fermentor was not included because the Propagation seed yeast counts were too low.

Two fermentors were analyzed and the empirical data of this Example is presented in the Tables below.

Example 7

Fine Milling of Corn and Whole Stillage Recycle

A process, designated Run #4278, according to the present invention was carried out in which the mash was prepared with finely milled corn. Moreover, the mash comprised 17% whole stillage recycle. The process of this Example is as follows:

Corn flour (1252 pounds/hour; 567.9 kg/hour) was conveyed into the Mix Tank (1500 gallon capacity; 5678 Liter capacity). The flour was made by grinding #2 yellow dent corn in a Bliss Model EX 1912 TF hammer mill using 0.125 inch (3.175 mm) (38% open area) opening screens. Process water (1674 pound/hour; 759.3 kg/hour) was added along with whole stillage (345 pounds/hour; 156.5 kg/hour) obtained from the adjacent commercial facility as back set. About 17% of the liquid added was whole stillage backset. The whole stillage used had 16.5% as-is basis total solids and 8.3% as-is insoluble solids. No thin stillage was added. Mix Tank residence time was 1.9 hours, the temperature was 145° F. (62.8° C.), and the pH was maintained at 5.2 without adjustment. 93.9% of the dry solids were estimated to be provided by the corn flour.

The slurry from the Mix Tank was pumped at a rate of 3143 pounds/hour (1425.6 kg/hour) to the Model M106AS HydroHeater steam-injection jet heater. A steam flow of 416 pounds/hour (188.7 kg/hour) of 150 psig (1034 kPa) saturated steam was measured to the HydroHeater to give a 296° F. (146.7° C.) jet exit temperature to paste the starch. The hold coil exit temperature was measured at 290° F. (143.3° C.) downstream of the jet. Pressures were 83.8 psig (577.8 kPa) at the inlet and 51.6 psig (355.8 kPa) at the exit of the hold coil. The flow residence time in the cook tube was about 10 minutes.

The hot mash was flash cooled after it exited the back pressure valve from the hold coil and entered the 300 gallon (1135.6 Liter) vacuum Flash Tank. The tank residence time was about 17 minutes. Ammonium hydroxide (26 Baume) was added to keep the pH at 5.9 and the temperature was maintained at 167° F. (75° C.) by vacuum cooling. α-amylase (5.0 mL/min; Novozyme Liquozyme) was added at a 0.00065 wt. enzyme/wt of dry solids dosage.

The enzyme-treated mash was then pumped at 6.5 gallons per minute (24.6 Liters per minute) to the 1100 gallon (4164 Liter) Liquefaction Tank for 90 minutes of nominal hold time at 180° F. (82.2° C.) to further liquefy the pasted starch.

The pH was adjusted to 5.0 using sulfuric acid after leaving the Liquefaction Tank and the temperature was lowered to 91° F. (32.8° C.) using plate and frame in-line coolers. Glucoamylase enzyme (6.0 mL/min.; Novozyme Spirizyme Fuel) enzyme was added continuously to the mash going to Propagation and Fermentation at this time for a 0.00074 wt. enz./wt. of dry solids dosage. The total solids were checked and inputs at the Mix tank adjusted to maintain 34.6% total solids as-is basis going to the Fermentors and Propagation.

The 300 gallon (1135.6 Liter) Propagation Tank was filled to the 245 gallon (927.4 Liter) mark with the cooled mash. Lactrol antibiotic (2 grams) was added plus Red Star yeast (1 pound; 453.6 grams) per Propagation tank. The Propagation tank was aerated with air (20 standard cubic feet per minute; 0.57 cubic meters per minute). The Propagation tank was pitched to the Fermentor at the 5% Fermentor fill level. Each Propagation Tank took about 45 minutes to fill and was pitched to the following Fermentor after 8 hours of fermentation time. Yeast counts in the two Propagation Tanks measured at transfer averaged: 385 million live, 146 million budding; 56 million dead for the two Prop Tanks analyzed for yeast counts. Propagation Tank C was not measured.

Three 8000 gallon (30,283 Liter) Fermentors were filled for 8 hours each. Urea solution (32% solids; 11 gallons (41.6 Liters)) was added to each fermentor at the 5% fill mark. No antibiotic was added to the fermentors. The fermentation temperature was maintained at 87.4° F. (30.8° C.) by cooling jackets with temperature control and the fermentors were agitated. Fermentor C was maintained at a higher temperature of 89.1° F. (31.7° C.). The fermentors were dropped to the beer well after 60 hours of fermentation and the amount of beer determined by totalizing the flow which yielded a range of 24,961 pounds (11,322 kg) to 25,569 pounds (11,598 kg) of beer for the fermentors.

Two of the fermentors had high residual starch and D-glucose in the beers and were excluded from the analysis. Fermentor A was analyzed and the empirical data of this Example is presented in the Tables below.

Example 8

Post-Liquefaction Enzymes

A process, designated Run #7008, according to the present invention was carried out in which enzymes were added post-liquefaction and prior to ethanol fermentation. The process of this Example is as follows:

Corn flour (1242 pounds/hour; 563.4 kg/hour) was conveyed into the Mix Tank (1500 gallon capacity; 5678 Liter capacity). The flour was made by grinding #2 yellow dent corn in a Bliss Model EX 1912 TF hammer mill using 0.125 inch (3.175 mm) (38% open area) opening screens. Process water (1589 pound/hour; 720.8 kg/hour) was added along with thin stillage (326 pounds/hour; 147.9 kg/hour) obtained from the adjacent commercial facility as back set. About 17% of the liquid added was thin stillage backset. The thin stillage used had a 9.30% as-is basis total solids and 1.50% as-is insoluble solids. No whole stillage was added. Mix Tank residence time was 1.8 hours, the temperature was 141° F. (60.6° C.), and the pH was maintained at 5.0 without adjustment. 96.5% of the dry solids were estimated to be provided by the corn flour to the Mix Tank.

The slurry from the Mix Tank was pumped at a rate of 3152 pounds/hour (1429.7 kg/hour) to the Model M106AS HydroHeater steam-injection jet heater. A steam flow of 404 pounds/hour (183.3 kg/hour) of 150 psig (1034 kPa) saturated steam was measured to the HydroHeater to give a 290° F. (143.3° C.) jet exit temperature to paste the starch. The hold coil exit temperature was measured at 275° F. (135° C.) downstream of the jet. Pressures were 58.6 psig (404.0 kPa) at the inlet and 46.0 psig (317.2 kPa) at the exit of the hold coil. The flow residence time in the cook tube was about 7 minutes.

The hot mash was flash cooled after it exited the back pressure valve from the hold coil and entered the 300 gallon (1135.6 Liter) vacuum Flash Tank. The tank residence time was about 25 minutes. Ammonium hydroxide (26 Baume) was added to keep the pH at 5.95 and the temperature was maintained at 187° F. (86.1° C.) by vacuum cooling. α-amylase (2.0 mL/min; Novozyme Liquozyme SC-DS) was added at a 0.00028 wt. enzyme/wt of dry solids dosage.

The enzyme-treated mash was then pumped at 5.4 gallons per minute (20.4 Liters per minute) to the 1100 gallon (4164 Liter) Liquefaction Tank for 99 minutes of nominal hold time at 182° F. (83.3° C.) to further liquefy the pasted starch. The total solids in the mash were checked and inputs at the Mix tank adjusted to maintain 34.1% total solids as-is basis going to the post-liquefaction and Propagation.

The pH was adjusted to 4.6 using sulfuric acid after leaving the Liquefaction Tank and the mash was sent to one of the 8000 gallon (30,283 Liter) Fermentors through the plate and frame heat exchanger and the temperature was lowered to 130° F. (54.4° C.). The post-liquefaction enzyme treatment was conducted in each Fermentor for the duration of the 16 hour fill time. Novozymes Viscozyme L carbohydrase (0.025%; 15 lb.); Genencor FermGen acid protease (0.001%; 0.6 lb.); and Genencor GC220 cellulase (15 lb.; 0.025%) enzymes were added to the Fermentor for the post-liquefaction treatment at the 15% tank fill (1550 gallon; 5867.4 Liter) level when the lower agitator in each Fermentor became flooded. The post-liquefaction treatment in Fermentor C was conducted at a low average temperature of 116° F. (46.7° C.) and became infected with lactic acid bacteria. For this reason it has been excluded from the analysis. No glucoamylase was added to the Fermentors until after the post-liquefaction treatment.

When the 16 hour fill was completed, the temperature in the Fermentor was reduced by applying cooling water to the tank jacket to reach 89° F. (31.7° C.) where it was maintained for the 60 hour saccharification and fermentation. The pH was adjusted to 4.5 if necessary and glucoamylase enzymes (1.27 gallons; 4.8 Liters; Novozymes Spirizyme Fuel) was added to each Fermentor for a 0.00071 wt. GA enz./wt. of dry solids dosage.

The 300 gallon (1135.6 Liter) Propagation Tank was filled to the 284 gallon (1075.1 Liter) mark with the cooled mash. Cooling water was applied to the jacket to reduce the temperature from 131° F. (55° C.) to 90° F. (32.2° C.) and the pH was adjusted to 4.5 before Lactrol antibiotic (3 g) were added plus Red Star yeast (3 pounds; 1.36 kg) per Propagation tank and glucoamylase enzyme (300 mL). The Propagation tank was aerated with air (20 standard cubic feet per minute; 0.57 cubic meters per minute). Urea solution (13 gallons; 49.2 Liters; 32% solids) was added to each Propagation Tank. Yeast growth was allowed to proceed for 12 hours before pitching the Propagation Tank to the Fermentor. 265 gallons (1003 Liters) of inoculum were pitched to the Fermentor and about 19 gallons (71.9 Liters) were lost as carbon dioxide, water vapor, and alcohol vapor from the Propagation tank prior to transfer. The Propagation tank was pitched to the Fermentor after the post-liquefaction treatment and the Fermentor pH and temperature were adjusted. Yeast counts in the two Propagation Tanks measured at transfer averaged: 647 million live, 247 million budding; 62 million dead for the two Prop Tanks analyzed for yeast counts. Propagation Tank A was not measured.

Three 8000 gallon (30,283 Liter) Fermentors were filled for 16 hours each. No urea or antibiotic was added directly to the fermentors. The fermentation temperature was maintained at 89.2° F. (31.8° C.) by cooling jackets with temperature control and the fermentors were agitated. Fermentor C was maintained at a lower temperature of 88.3° F. (31.3° C.). The two fermentors analyzed were dropped to the beer well after 60 hours of fermentation and the amount of beer determined by totalizing the flow which yielded a range of 43,770 pounds (19,854 kg) to 46,987 pounds (21,313 kg) of beer for the fermentors.

Fermentor C had high lactic acid and was excluded from the analysis. Fermentors A and D were analyzed and the empirical data of this Example is presented in the Tables below.

Example 9

Control Experiment

A control experiment, designated Run #7016, was carried out without the post-liquefaction enzymes. The experimental conditions are as follows:

Corn flour (1294 pounds/hour; 586.9 kg/hour) was conveyed into the Mix Tank (1500 gallon capacity; 5678 Liter capacity). The flour was made by grinding #2 yellow dent corn in a Bliss Model EX 1912 TF hammer mill using 0.125 inch (3.175 mm) (38% open area) opening screens. Process water (1578 pounds/hour; 715.8 kg/hour) was added with thin stillage (302 pounds/hour; 137) obtained from the adjacent commercial facility as back set. About 16.1% of the liquid added was thin stillage backset. The thin stillage used had 8.31% as-is basis total solids and 0.79% as-is insoluble solids. No whole stillage was added. Mix Tank residence time was 1.8 hours, the temperature was 139° F. (59.4° C.), and the pH was maintained at 5.0 without adjustment. 97.2% of the dry solids were estimated to be provided by the corn flour to the Mix Tank.

The slurry from the Mix Tank was pumped at a rate of 3127 pounds/hour (1418.4 kg/hour) of to the Model M106AS HydroHeater steam-injection jet heater. A steam flow of 426 pounds/hour (193.2 kg/hour) of 150 psig (1034 kPa) saturated steam was measured to the HydroHeater to give a 290° F. (143.3° C.) jet exit temperature to paste the starch. The hold coil exit temperature was measured at 280° F. (137.8° C.) downstream of the jet. Pressures were 70.3 psig (484.7 kPa) at the inlet and 47.8 psig (329.6 kPa) at the exit of the hold coil. The flow residence time in the cook tube was about 7 minutes.

The hot mash was flash cooled after it exited the back pressure valve from the hold coil and entered the 300 gallon (1135.6 Liter) vacuum Flash Tank. The tank residence time was about 25 minutes. Ammonium hydroxide (26 Baume) was added to keep the pH at 6.11 and the temperature was maintained at 185.5° F. (85.3° C.) by vacuum cooling. α-amylase (2.0 mL/min; Novozyme Liquozyme SC-DS) was added at a 0.00028 wt. enzyme/wt of dry solids dosage.

The enzyme-treated mash was then pumped at 5.34 gallons per minute (20.21 Liters per minute) to the 1100 gallon (4164 Liter) Liquefaction Tank for 87.3 minutes of nominal hold time at 181° F. (82.8° C.) to further liquefy the pasted starch.

The pH was adjusted to 4.5 using sulfuric acid after leaving the Liquefaction Tank and the temperature was lowered to 90° F. (32.2° C.) using plate and frame in-line coolers. Glucoamylase enzyme (6.0 mL/min.; Novozyme Spirizyme Fuel) enzyme was added continuously to the cooled mash going to Propagation and Fermentation at this time for a 0.00071 wt. enz./wt. of dry solids dosage. The total solids were checked and inputs at the Mix tank adjusted to maintain 34.8% total solids as-is basis going to the Fermentors and Propagation.

The 300 gallon (1135.6 Liter) Propagation Tank was filled to the 285 gallon (1078.8 Liter) mark with the cooled mash. Lactrol antibiotic (3 grams) was added plus Red Star yeast (3 pound; 1.36 kg) per Propagation tank. The Propagation tank was aerated with air (20 standard cubic feet per minute; 0.57 cubic meters per minute). The Propagation tank was pitched to the Fermentor at the 5% Fermentor fill level. 245 gallons (927.4 Liters) of inoculum were pitched to the Fermentor and about 40 gallons (151 Liters) were lost as carbon dioxide, water vapor, and alcohol vapor from the Propagation tank prior to transfer. Each Propagation Tank took about 45 minutes to fill and was pitched to the following Fermentor after 12 hours of fermentation time. Yeast counts in the Propagation Tank at transfer were: 642 million live, 334 million budding; 65 million dead.

Three 8000 gallon (30,283 Liter) Fermentors were filled for 15 hours each. Urea solution (32% solids; 13 gallons (49.2 Liters)) was added to each fermentor at the 5% fill mark. No antibiotic was added to the fermentors. The fermentation temperature was maintained at 91° F. (32.8° C.) by cooling jackets with temperature control and the fermentors were agitated. The fermentors were dropped to the beer well after 60 hours of fermentation and the amount of beer determined by totalizing the flow and/or from the volume in the tanks prior to the drop yielded a range of 44,390 pounds (20,135 kg) to 47,083 pounds (21,356 kg) of beer for the two fermentors retained in the yield analysis. The third fermentor was not included because the residual starch and sugars were very high and the alcohol low. The temperature control for the first 5 hours of fermentation was far out of range for this fermentor (D) and shock to the yeast is thought to have occurred.

Two fermentors were analyzed and the empirical data of this Example is presented in the Tables below.

TABLE 1

Flour Mean Particle Sizes

| Run | Mill Screen Size (inches/mm) | Flour mean particle size, measured internally (micrometers) | Flour mean particle size, measured by Outside Lab (micrometers)* |
|---|---|---|---|
| #4139 | 0.125 inch/3.175 mm | 808.4 | 590.1 |
| #4146 | 0.25 inch/6.35 mm | 608.3 | NM |
| #4150 | 0.25 inch/6.35 mm | 848.6 | 586.5 |
| #4209 | 0.25 inch/6.35 mm | 878.4 | 621.1 |
| #4211 | 0.25 inch/6.35 mm | 794.1 | NM |
| #4255 | 0.125 inch/3.175 mm | 1152.3 | 598.6 |
| #4278 | 0.125 inch/3.175 mm | 942.5 | NM |
| #7008 | 0.125 inch/3.175 mm | 704.5 | NM |
| #7016 | 0.125 inch/3.175 mm | 677.9 | NM |

*NM = not measured

TABLE 2

Flour Dry Solids Content

| Run | Dry solids content (wt. %), measured internally | Dry solids content (wt. %), measured by Outside Lab* |
|---|---|---|
| #4139 | 87.9 | 86.8 |
| #4146 | 91.1 | NM |
| #4150 | 87.3 | 87.4 |
| #4209 | 87.7 | 88.4 |
| #4211 | 89.9 | NM |
| #4255 | 89.6 | 87.8 |
| #4278 | 88.2 | 85.8 |
| #7008 | 85.2 | 84.8 |
| #7016 | 85.3 | 84.9 |

*NM = not measured

TABLE 3

Corn Flour Nutrition

| Run | Crude Protein, % DB | ADICP, % DB | Crude Fat, % DB | Ash, % DB |
|---|---|---|---|---|
| #4139 | 8.58 | 0.45 | 3.85 | 1.29 |
| #4146 | NM | NM | NM | NM |
| #4150 | 8.10 | 0.30 | 3.95 | 1.24 |
| #4209 | 8.59 | 0.35 | 3.95 | 1.40 |
| #4211 | NM | NM | NM | NM |
| #4255 | 8.6 | 0.5 | 3.6 | 1.2 |
| #4278 | 9.2 | 0.8 | 3.9 | 1.3 |
| #7008 | 8.3 | NM | 3.5 | 1.3 |
| #7016 | 8.7 | NM | 2.6 | 3.7 |

% DB = % Dry Basis
ADICP = Acid Detergent Insoluble Crude Protein

| Run | ADF, % DB | NDF, % DB | Crude Fiber, % DB | Starch, % DB |
|---|---|---|---|---|
| #4139 | 2.25 | 9.25 | NM | 74.59 |
| #4146 | NM | NM | NM | 74 (est.) |
| #4150 | 2.35 | 10.25 | NM | 74 (est.) |
| #4209 | 2.60 | 10.55 | NM | 74 (est.) |
| #4211 | NM | NM | NM | 74 (est.) |
| #4255 | 2.8 | 11.9 | NM | 72.1 |
| #4278 | 3.6 | 19.4 | NM | 68.2 |
| #7008 | 3.6 | 10.0 | 2.6 | 70.7 |
| #7016 | 0.7 | 3.3 | 13.8 | 71.3 |

% DB = % Dry Basis
ADF = Acid Detergent Fiber
NDF = Neutral Detergent Fiber

TABLE 4

Ethanol Content of Beer and Ethanol Yield

| Run | Mean Ethanol Content in Beer (wt. %, correct) | Content Standard Deviation | Yield, (kg ethanol per kg corn dry solids) | Yield Standard Deviation |
|---|---|---|---|---|
| #4139 | 12.66 | 0.49 | 0.347 | 0.009 |
| #4146 | 12.56 | 0.33 | 0.362 | 0.021 |
| #4150 | 12.31 | 0.42 | 0.358 | 0.012 |
| #4209 | 14.43 | 0.34 | 0.404 | 0.003 |
| #4211 | 12.61 | 0.20 | 0.398 | 0.020 |
| #4255 | 12.88 | 0.20 | 0.358 | 0.006 |
| #4278 | 13.27 | — | 0.366 | — |
| #7008 | 13.66 | 0.12 | 0.369 | 0.0006 |
| #7016 | 13.37 | 0.001 | 0.359 | 0.011 |

TABLE 4

Solids Content of Beer

| Run | Total solids, wt. % | Standard deviation of Total Solids, wt. % | Insoluble Solids, wt. % | Standard deviation of Insoluble Solids, wt. % |
|---|---|---|---|---|
| #4139 | 11.36 | 0.625 | 5.53 | 0.515 |
| #4146 | 11.81 | 2.378 | 5.25 | 1.006 |
| #4150 | 10.78 | 1.540 | 5.31 | 0.716 |
| #4209 | 10.69 | 1.049 | 4.64 | 0.031 |
| #4211 | 10.71 | 0.786 | 3.65 | 0.527 |
| #4255 | 10.14 | 2.067 | 4.12 | 1.245 |
| #4278 | 12.47 | — | 5.94 | — |
| #7008 | 12.13 | 0.558 | 5.98 | 0.100 |
| #7016 | 12.81 | 0.322 | 6.69 | 0.475 |

TABLE 5

Beer Solids Nutrition

| Run | Crude Protein, % DB | ADF, % DB | NDF, % DB | Crude Fiber, % DB |
|---|---|---|---|---|
| #4139 | 32.2 | 13.75 | 36.8 | NM |
| #4146 | NM | NM | NM | NM |
| #4150 | 30.1 | 11.9 | 34.15 | NM |
| #4209 | 31.85 | 15.75 | 36.05 | NM |
| #4211 | NM | NM | NM | NM |
| #4255 | 30.75 | 13.4 | 32.6 | NM |
| #4278 | 32.7 | 14.7 | 34 | NM |
| #7008 | 29.7 | 11.85 | 22.1 | NM |
| #7016 | 30.35 | 14.5 | 24 | 9.2 |

% DB = % Dry Basis
ADF = Acid Detergent Fiber
NDF = Neutral Detergent Fiber

| Run | Crude Fat, % DB | Ash, % DB | Starch and Sugars, % DB | Water Insoluble Starch, % DB |
|---|---|---|---|---|
| #4139 | 12.6 | 8.80 | 1.9 | NM |
| #4146 | NM | NM | NM | NM |
| #4150 | 10.55 | 9.35 | 7.42 | NM |
| #4209 | 12.5 | 11.03 | 1.02 | NM |
| #4211 | NM | NM | NM | NM |
| #4255 | 11.45 | 5.24 | 0.87 | NM |
| #4278 | 12.5 | 5.17 | 0.85 | NM |
| #7008 | 6.4 | 6.06 | 3.27 | 1.61 |
| #7016 | 11.4 | 7.00 | 5.63 | 2.92 |

% DB = % Dry Basis

Runs #4139, #4145, #4150, and #7106 are control experiments. The ethanol yields (in terms of kg ethanol per kg corn dry solids) for these experiments were 0.347, 0.362, 0.358, and 0.359, respectively. The average yield of these four runs is therefore 0.3565 kg ethanol per kg corn dry solids. Runs #4209, #4211, #4255, #4278, and #7008 are experiments based on methods of the present invention, even though the conditions were varied. The ethanol yields (in terms of kg ethanol per kg corn dry solids) for these experiments were 0.404, 0.398, 0.358, and 0.366, and 0.369 respectively. The average yield of these five runs is therefore 0.379 kg ethanol per kg corn dry solids. The ethanol yield increase for the five examples according to the present invention was therefore 6.3% higher than the four control runs. The methods of Examples 4 and 5, both of which incorporated whole stillage recycle, gave the largest increases in ethanol yield.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above compositions and processes without departing from the scope of the invention, it is intended that all matter contained in the above description and shown in the accompanying drawing shall be interpreted as illustrative and not in a limiting sense.

What is claimed is:

1. A process for producing a modified feed co-product by ethanol fermentation of plant matter, the process comprising:
    forming an acidic aqueous medium comprising said plant matter and having a pH from about 2 to about 6, said plant matter comprising starch and another polysaccharide selected from the group consisting of hemicellulose and cellulose;
    hydrolyzing at least a portion of the starch, said another polysaccharide, or both in said medium a temperature of at least 85° C.;
    contacting at least a portion of said starch in said acidic aqueous medium with α-amylase which catalyzes enzymatic hydrolysis of at least a portion of the starch to yield simple sugars having from one to three saccharide units;
    contacting said another polysaccharide in said acidic aqueous medium with a primary pre-conversion enzyme selected from the group consisting of xylanase, cellulase, hemicellulase, and combinations thereof, the primary pre-conversion enzyme catalyzing enzymatic hydrolysis of at least a portion of said another polysaccharide to yield a primary enzymatic hydrolyzate containing additional simple sugars having from one to four saccharide units;
    combining the primary enzymatic hydrolysate and a yeast to thereby form a primary fermentation mixture, wherein at least a portion of the simple sugars produced by hydrolysis of said starch and said another polysaccharide are converted by fermentation to produce ethanol;
    distilling the primary fermentation mixture to separate at least a portion of the ethanol thereby forming: (i) a primary distillate product comprising ethanol; and (ii) a primary feed co-product derived from the fermentation of the primary fermentation mixture, the primary feed co-product comprising at least a portion of said another polysaccharide selected from the group consisting of hemicellulose and cellulose remaining therein;
    forming an acidified primary feed co-product by adjusting the pH of the primary feed co-product to between about 2.5 and 5.0;
    forming a hydrolyzed primary feed co-product, the said forming comprising hydrolyzing at least a portion of the another polysaccharide remaining in said acidified primary feed co-product at a temperature of at least 85° C.;
    combining the hydrolyzed primary feed co-product, a secondary pre-conversion enzyme, and a pH adjusting agent to form a secondary enzymatic hydrolysate having a pH from about 4 to about 6.5, wherein the secondary pre-conversion enzyme is selected from the group consisting essentially of cellulase, hemicellulase, and combinations thereof, and wherein the secondary pre-conversion enzyme catalyzes enzymatic hydrolysis of at least a portion of the another polysaccharide remaining in said secondary enzymatic hydrolysate to produce a third crop of simple sugars having from one to four saccharide units;
    adding yeast to the secondary enzymatic hydrolysate to form a secondary fermentation mixture such that at least a portion of the simple sugars contained therein are converted by fermentation to produce ethanol; and
    distilling the secondary fermentation mixture to separate at least a portion of the ethanol thereby forming (i) the modified feed co-product and (ii) a secondary distillate product comprising ethanol.

2. The process of claim 1 wherein the plant matter comprises a feed co-product derived from fermentation of fruit or seeds of an energy crop to produce ethanol, wherein the feed co-product is selected from the group consisting of whole stillage, thin stillage, condensates of whole stillage, and condensates of thin stillage.

3. The process of claim 1 wherein the primary enzymatic hydrolysate is further combined with a glucoamylase.

4. The process of claim 1 wherein the glucoamylase is combined with the primary enzymatic hydrolysate prior to combining the primary enzymatic hydrolysate with yeast.

5. The process of claim 1 wherein the hydrolyzed primary feed coproduct is further combined with a glucoamylase.

6. The process of claim 1 wherein the glucoamylase is combined with the secondary enzymatic hydrolysate prior to combining the secondary enzymatic hydrolysate with yeast.

7. The process of claim 1 wherein the plant matter is derived from corn.

8. The process of claim 7 wherein the ethanol obtained by combining the primary distillate product and the secondary distillate product is at least 2.7 gallons of ethanol per bushel of corn.

9. The process of claim 1 wherein the modified feed co-product comprises at least 32 weight % protein on a dry weight basis.

10. The process of claim 1 wherein the acidic aqueous medium comprising plant matter is hydrolyzed at a pH between about 2 and about 4 and the acidic aqueous liquid medium pH is adjusted to between about 4 and about 6.5 prior to contact with α-amylase.

11. The process of claim 1 comprising hydrolyzing the acidic aqueous medium at a temperature of between about 120° C. and about 160° C. to hydrolyze at least a portion of said another polysaccharide followed by cooling to between about 70° C. and about 90° C. prior to contact with α-amylase.

12. The process of claim 2 wherein the feed co-product is selected from the group consisting of whole stillage and thin stillage, wherein the whole stillage and thin stillage comprise insoluble solids.

13. The process of claim 1 wherein the acidified primary feed co-product is adjusted to a pH of between about 2.5 and about 4.5, the acidified primary feed co-product is hydrolyzed at a temperature of between 85° C. and 200° C., and the hydrolyzed acidified primary feed co-product, the secondary pre-conversion enzyme, and the pH adjusting agent are combined to form a secondary enzymatic hydrolysate having a pH of from 5 to 6.5.

* * * * *